US012780775B2

(12) United States Patent
Hoepping et al.

(10) Patent No.: US 12,780,775 B2
(45) Date of Patent: Nov. 3, 2026

(54) IODOTYROSINE DERIVATIVES AND PROCESS FOR PREPARING IODOTYROSINE DERIVATIVES

(71) Applicant: ABX ADVANCED BIOCHEMICAL COMPOUNDS—BIOMEDIZINISCHE FORSCHUNGSREAGENZIEN GMBH, Radeberg (DE)

(72) Inventors: Alexander Hoepping, Radeberg (DE); Christoph Meyer, Radeberg (DE); Desna Joseph, Radeberg (DE); Stefan David Köster, Radeberg (DE); Erik Eiselt, Radeberg (DE)

(73) Assignee: ABX ADVANCED BIOCHEMICAL COMPOUNDS—BIOMEDIZINISCHE FORSCHUNGSREAGENZIEN GMBH, Radeberg (DE)

( * ) Notice: Subject to any disclaimer, the term of this patent is extended or adjusted under 35 U.S.C. 154(b) by 582 days.

(21) Appl. No.: 18/255,119

(22) PCT Filed: Nov. 30, 2021

(86) PCT No.: PCT/EP2021/083649
§ 371 (c)(1),
(2) Date: May 31, 2023

(87) PCT Pub. No.: WO2022/117590
PCT Pub. Date: Jun. 9, 2022

(65) Prior Publication Data

US 2024/0067599 A1 Feb. 29, 2024

(30) Foreign Application Priority Data

Dec. 1, 2020 (EP) .................................... 20211107

(51) Int. Cl.
*C07C 229/36* (2006.01)
*C07C 227/16* (2006.01)

(52) U.S. Cl.
CPC .......... *C07C 229/36* (2013.01); *C07C 227/16* (2013.01)

(58) Field of Classification Search
None
See application file for complete search history.

(56) References Cited

U.S. PATENT DOCUMENTS

2011/0178302 A1 7/2011 Satyamurthy et al.

FOREIGN PATENT DOCUMENTS

EP 1116727 A1 7/2001
WO 2010008522 A2 1/2010

OTHER PUBLICATIONS

English translation of PCT search report mailed Feb. 9, 2022 (Year: 2022).*
Giroud et al. (J. Med. Chem., 2018, 61, 3370) (Year: 2018).*
Greene's Protective Groups in Organic Synthesis (4th Ed., Wuts and Greene, 2007, John Wiley). (Year: 2007).*
Office Action issued on Sep. 13, 2023, in corresponding European Application No. 20211107.6, 10 pages.
Office Action issued on Dec. 11, 2024, in corresponding Japanese Application No. 2023-532457, 9 pages.
Office Action issued on Feb. 7, 2025, in corresponding Korean Application No. 10-2023-7022122, 13 pages.
International Preliminary Report on Patentability issued on May 30, 2023, in corresponding International Application No. PCT/EP2021/083649, 7 pages.
Office Action issued on Sep. 11, 2025, in corresponding Chinese Application No. 202180080892.9, 16 pages.
Office Action issued on Oct. 21, 2025, in corresponding Korean Application No. 10-2023-7022122, 24 pages.
Office Action issued on Jul. 9, 2025 , in corresponding Japanese Application No. 2023-532457, 6 pages.
Office Action issued on May 13, 2025, in corresponding European Application No. 20211107.6, 6 pages.
Office Action issued on May 23, 2025, in corresponding European Application No. 21815222.1, 8 pages.
Office Action issued on Apr. 24, 2024, in corresponding Japanese Application No. 2023-532457, 12 pages.
Giroud et al., "Repurposing a Library of Human Cathepsin L Ligands: Identification of Macrocyclic Lactams as Potent Rhodesain and Trypanosoma Brucei Inhibitors", Journal of Medicinal Chemistry, American Chemical Society, ACS Publications, 2018, vol. 61, 20 pages.

(Continued)

*Primary Examiner* — Renee Claytor
*Assistant Examiner* — Jennifer C Sawyer
(74) *Attorney, Agent, or Firm* — Maier & Maier, PLLC

(57) ABSTRACT

A compound of general formula I (formula I)

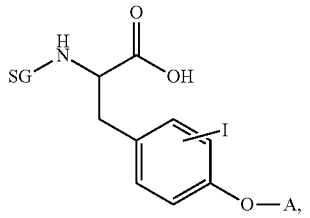

wherein A is selected from the group of an unbranched or branched alky group with 1 to 12 carbon atoms, an —$R^1$—O—$R^2$ group, an —$R^1$—Si($R^3R^4R^5$) group, an —$R^1$—O—Si($R^3R^4R^5$) group, a —C(O)—O—$R^9$—Si($R^3R^4R^5$) group, a —CH(O—$R^6$)(O—$R^7$) group, an —$R^1$—CH(O—$R^6$)(O—$R^7$) group, or an —$R^1$—O—C(O)—O—$R^8$ group; SG is a protective group; $R^1$ is a divalent hydrocarbon residue with 1 to 12 carbon atoms; $R^2$ is a monovalent hydrocarbon residue with 1 to 12 carbon atoms; $R^3$, $R^4$ and $R^5$ each independently are a monovalent hydrocarbon residue with 1 to 12 carbon atoms; $R^6$ and $R^7$ each independently are a monovalent hydrocarbon residue with 1 to 12 carbon atoms; $R^8$ is a monovalent hydrocarbon residue with 1 to 12 carbon atoms; and $R^9$ is a divalent hydrocarbon residue with 1 to 12 carbon atoms.

11 Claims, No Drawings

(56) References Cited

OTHER PUBLICATIONS

Greene et al., "Protective Groups in Organic Synthesis", A Wiley-Interscience Publication, John Wiley & Sons, Inc., 1999, Third Edition, 22 pages.
Office Action issued on Mar. 10, 2025, in corresponding Chinese Application No. 202180080892.9, 16 pages.
CAS STNex, STN database, Chemcats, CAS RN 1379870-13-9 Registry, Jun. 25, 2012, CAS RN 1259991-52-0 Registry, Jan. 19, 2011, American Chemical Society, 2 pages.
International Search Report and Written Opinion issued on Feb. 9, 2022, in corresponding International Application No. PCT/EP2021/083649, 14 pages.
Steer et al., "A direct route for the preparation of Fmoc/OtBu protected iodotyrosine", Tetrahedron Letters , 2018, vol. 59, No. 27, pp. 2644-2646.
White et al., "Total synthesis of geodiamolide A, a novel cyclodepsipeptide of marine origin", The Journal of Organic Chemistry, 1989, vol. 54, No. 4, pp. 736-738.
Ng-Choi et al., "Solid-phase synthesis of biaryl cyclic peptides containing a histidine-tyrosine linkage", Tetrahedron, 2019, vol. 75, No. 18, pp. 2625-2636.
Krenitsky et al., "Synthesis of the (S, S, S)-diastereomer of the 15-membered biaryl ring system of RP 66453", Tetrahedron letters, 2003, vol. 44, No. 21, pp. 4019-4022.
Tóth et al., "The site-specific basicity of thyroid hormones and their precursors as regulators of their biological functions", Journal of pharmaceutical and biomedical analysis, 2012, vol. 61, pp. 156-164.

* cited by examiner

IODOTYROSINE DERIVATIVES AND PROCESS FOR PREPARING IODOTYROSINE DERIVATIVES

FIELD

The invention relates to iodotyrosine derivatives, in particular Fmoc-3-iodotyrosine derivatives and boc-3-iodotyrosine derivatives. Furthermore, it relates to a method for the preparation of iodotyrosine derivatives, in particular of Fmoc-3-iodotyrosine derivatives and boc-3-iodotyrosine derivatives. In addition, it relates to the use of iodotyrosine derivatives, in particular of Fmoc-3-iodotyrosine derivatives and boc3-iodotyrosine derivatives, in the synthesis of peptides.

BACKGROUND

Modification of peptides with 3-iodotyrosine (D/L) substantially is to positively affect the properties of the iodotyrosine bearing peptides. In many cases, iodotyrosine is introduced at the N-terminal end of peptides or small molecules [4]. Due to the lipophilic nature of iodotyrosine binding properties are improved, which often results in improved receptor affinities. Examples of peptides or peptide compounds containing iodotyrosine are the theranostic peptide pair Pentixather/Pentixafor [5], HA-DOTATATE [6] or PSMA I&T [7]. Furthermore, substitution of tyrosine by iodotyrosine results in improved properties of e.g. hormones [8].

In most cases, iodotyrosine is introduced using the commercially available building blocks Fmoc-3-iodo-L-tyrosine, Fmoc-3-iodo-D-tyrosine, boc-3-iodo-D-tyrosine, or boc-3-iodo-L-tyrosine. Here, "Fmoc" designates the protective group fluorenylmethyloxycarbonyl. Boc designates the protective group tert-butyloxycarbonyl. However, using Fmoc-3-iodo-L-tyrosine, Fmoc-3-iodo-D-tyrosine, boc-3-iodo-D-tyrosine, or boc-3-iodo-L-tyrosine may be associated with undesired side reactions, since their hydroxy functionality in the para position is still sufficiently nucleophilic to be acylated by C-terminally activated amino acids. In most cases, this results in the loss of the amino acid which is no longer available for coupling. In this context, couplings with Fmoc-3-iodo-L-tyrosine, Fmoc-3-iodo-D-tyrosine, boc-3-iodo-D-tyrosine, or boc-3-iodo-L-tyrosine induced by the high reactivity of the nucleophilic hydroxy functionality of tyrosine have not proved to be practicable if there is only a low or no conversion in said reaction step.

One way to overcome said drawback is to iodize tyrosine in the peptide end product. Said processing mode typically results in two different products consisting of a mono-iodized tyrosine residue and a di-iodized tyrosine residue [9]. Both have to be separated by means of reversed-phase chromatography which makes industrial application difficult. Furthermore, said method is not suitable if more than one tyrosine entity is present in the peptide. Furthermore, said method is not suitable for industrial application, since the synthesis scale is clearly limited. In addition, the starting material has to be separated.

Cobb et al. suggest the direct iodization of completely protected Fmoc-Tyr(tBu)-OH in the presence of $Ag_2SO_4$ in methanol, which mainly results in Fmoc-3-iodo-Tyr(tBu)-OMe, followed by saponification. Said method is considered to be unsuitable for larger scales as needed in industrial applications. Amedio et al. [11] represented the use of boc-3-iodo-Tyr(PMB)-OH. In a further example, Kiyoyuki et al. used boc-3-iodo-Tyr(boc)-OH for the synthesis of a cyclic peptide [12]. Both protected iodotyrosine derivatives are exclusively suitable for boc chemistry. Martiny et al. synthesized Fmoc-3-iodo-Tyr(TBDMS)-OH, which has proved to be suitable for the introduction of iodized tyrosines into peptides by means of Fmoc/tBu chemistry [13]. The drawback of said specific compound is the susceptibility with respect to (weak) acids (e.g., hexafluoroisopropanol (HFIP)). Said susceptibility may result in the failure to cleave off the peptides completely protected from the resin (e.g., using HFIP). Here, "tBu" designates the protective group "tert-butyl", "Me" methyl, "boc" the protective group tert-butoxycarbonyl, "PMB" the protective group p-methoxybenzyl, "TBDMS" the protective group "tert-butyldimethylsilyl".

SUMMARY

The problem of the invention is to eliminate the drawbacks according to the prior art. Provided are iodotyrosine derivatives, in particular Fmoc-3-iodotyrosine derivatives, and boc-3-iodotyrosine derivatives, which do not hinder the modification of peptides by introducing an iodotyrosine entity without the described side reactions and the cleavage of peptides modified in this way in the completely protected state of a resin.

Said problem is solved by the features of claims 1, 9, and 12. Suitable developments of the inventions result from the features of the dependent claims.

In accordance with the invention there is provided a compound of general formula I (formula I)

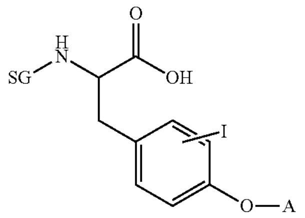

wherein

A is selected from the group consisting of an unbranched or branched alkyl group with 1 to 12 carbon atoms, an $—R^1—O—R^2$ group, an $—R^1—Si(R^3R^4R^5)$ group, an $—R^1—O—Si(R^3R^4R^5)$ group, a $—C(O)—O—R^9—Si(R^3R^4R^5)$ group, a $—CH(O—R^6)(O—R^7)$ group, an $—R^1—CH(O—R^6)(O—R^7)$ group, an $—R^1—O—C(O)—O—R^8$ group;

SG is a protective group;

$R^1$ is a divalent hydrocarbon residue with 1 to 12 carbon atoms;

$R^2$ is a monovalent hydrocarbon residue with 1 to 12 carbon atoms;

$R^3$, $R^4$, and $R^5$ each independently are a monovalent hydrocarbon residue with 1 to 12 carbon atoms;

$R^6$ and $R^7$ each independently are a monovalent hydrocarbon residue with 1 to 12 carbon atoms;

$R^8$ is a monovalent hydrocarbon residue with 1 to 12 carbon atoms; and $R^9$ is a divalent hydrocarbon residue with 1 to 12 carbon atoms.

Protective group SG is preferably selected from the group consisting of a fluorenylmethyloxycarbonyl group (Fmoc), a tert-butoxycarbonyl group (boc), and a benzyloxycarbonyl group. More preferably, the protective group SG is fluorenylmethyloxycarbonyl (Fmoc) or tert-butoxycarbonyl. Particularly preferred the protective group SG is fluorenylmethyloxycarbonyl (Fmoc). The protective group SG is for protecting the amino function of the tyrosine entity. The compounds of general formula I in the following are also referred to as SG iodotyrosines.

A compound of general formula I in which SG is a fluorenylmethyloxycarbonyl group (Fmoc) is a compound of general formula Ia; a compound of general formula I in which SG is a tert-butoxycarbonyl group (boc) is a compound of general formula Ib:

formula Ia

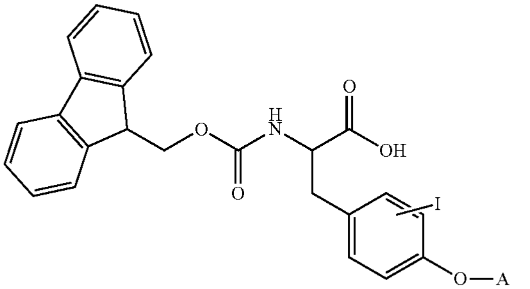

formula Ib

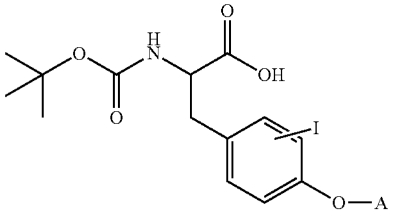

The compounds of general formula Ia in the following are also referred to as Fmoc-iodotyrosines. The compounds of general formula Ib in the following are also referred to as boc-iodotyrosines.

The compound of general formula I according to the invention comprises both each of the enantiomers in itself and mixtures of said enantiomers. Thus, the tyrosine entity of the compound of general formula I may be present in the D configuration, in the L configuration, or as a mixture of the D and L configurations. "D/L" designates a compound present in the D configuration, in the L configuration, or as a mixture of the D and L configurations.

The compound of general formula I according to the invention has an iodine atom bound to the phenyl group of the tyrosine entity.

The compounds according to the invention permit the introduction of SG-3-iodo-D-tyrosine(A)-OH or SG-3-iodo-L-tyrosine(A)-OH into peptides. The protection of the phenolic hydroxy group by the protective group A prevents the undesired side reactions which according to the prior art are associated with the unprotected hydroxy functionality. Thus, entity A prevents acylation by C-terminally activated amino acids. Thus, loss of amino acid is prevented. Moreover, now difficult couplings with SG-3-iodo-D-tyrosine(A)-OH or SG-3-iodo-L-tyrosine(A)-OH can be performed, because the phenolic hydroxy functionality is protected by means of entity A. In particular, the invention permits introduction of Fmoc-3-iodo-D-tyrosine(A)-OH or Fmoc-3-iodo-L-tyrosine (A)-OH into peptides. Furthermore, it permits introduction of boc-3-iodo-D-tyrosine(A)-OH or boc-3-iodo-L-tyrosine (A)-OH into peptides. "(A)-OH" shall indicate that the phenolic hydroxy group of the tyrosine entity is protected by protective group A, but the hydroxy group of the carboxy group is not protected. Once having introduced SG-3-iodo-D-tyrosine(A)-OH or SG-3-iodo-L-tyrosine(A)-OH into a peptide protective group A can be cleaved off.

It may be provided that the compound of general formula I is a compound of general formula I-A (formula I-A)

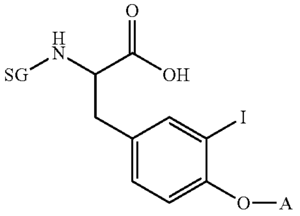

wherein A has the meanings given in claim 1. The compound of general formula I-A corresponds to the compound of general formula I except that the iodine atom is in the 3 position. A compound of general formula I-A in which SG is a fluorenylmethyloxycarbonyl group (Fmoc) is a compound of general formula Ia-A; a compound of general formula I in which SG is a tert-butoxycarbonyl group (boc) is a compound of general formula Ib-A:

formula Ia-A

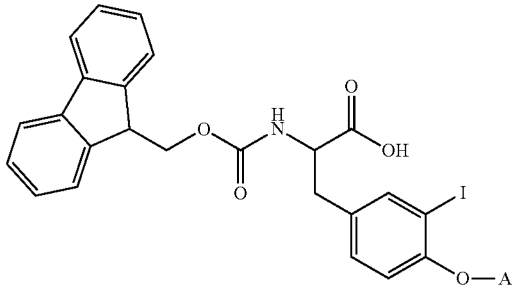

formula Ib-A

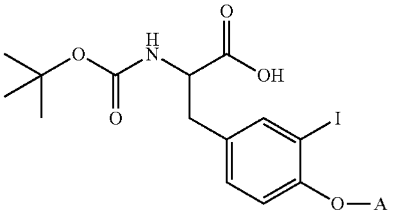

Entity A is a protective group to protect the phenolic hydroxy group of SG iodotyrosine. Entity A preferably is an ether group, a silylether group, an acetal group, or a carbonate group. In case of Fmoc-iodotyrosine entity A is preferably selected such that it is compatible with the Fmoc/tBu strategy, as applied with non-iodized Fmoc-D/L-tyrosine(tBu)-OH. In Fmoc-D/L-tyrosine(tBu)-OH the phenolic hydroxy functionality is protected by a tert-butyl group (tBu). Moreover, entity A is selected such that the compound according to the invention can be used in the production scale.

$R^1$ is preferably an unbranched alkylene group with 1 to 6 methylene entities. Preferably, $R^1$ is methylene, ethylene, or n-propylene.

$R^2$ is preferably an unbranched or branched alkyl group with 1 to 12 carbon atoms or an aryl group, with an unbranched or branched alkyl group with 1 to 12 carbon atoms being preferred.

Preferably, $R^3$, $R^4$, and $R^5$ each independently are an unbranched or branched alkyl group with 1 to 2 carbon atoms or an aryl group.

Preferably, $R^6$ and $R^7$ each independently are an unbranched or branched alkyl group with 1 to 2 carbon atoms or an aryl group.

$R^8$ is preferably an unbranched or branched alkyl group with 1 to 12 carbon atoms or an aryl group with an unbranched or branched alkyl group with 1 to 12 carbon atoms being preferred.

$R^9$ is preferably an unbranched alkylene group with 1 to 6 methylene entities. Preferably, $R^1$ is methylene, ethylene, propylene, or butylene.

It may be provided that the entity A is selected from the group consisting of an unbranched or branched alkyl group with 1 to 12 carbon atoms, an —$R^1$—O—$R^2$ group, an —$R^1$—Si($R^3R^4R^5$) group, and an —C(O)—O—$R^9$—Si ($R^3R^4R^5$) group. It may be provided that the entity A is selected from the group consisting of an —$R^1$—O—$R^2$ group, an —$R^1$—Si($R^3R^4R^5$) group, an —$R^1$—O—Si ($R^3R^4R^5$) group, a —C(O)—O—$R^9$—Si($R^3R^4R^5$) group, a —CH(O—$R^6$)(O—$R^7$) group, an —$R^1$—CH(O—$R^6$)(O—$R^7$) group, an —$R^1$—O—C(O)—O—$R^8$ group. It may further be provided that the entity A is selected from the group consisting of an alkyl group with 1 to 6 carbon atoms; an —$R^1$—O—$R^2$ group in which $R^1$ is an alkylene group with 1 to 6 carbon atoms; and $R^2$ is an unbranched or branched alkyl group with 1 to 6 carbon atoms;

an —$R^1$—Si($R^3R^4R^5$) group in which $R^1$ is an alkylene group with 1 to 6 carbon atoms; and $R^3$, $R^4$, and $R^5$ each independently are an unbranched or branched alkyl group with 1 to 6 carbon atoms or an aryl group; and a —C(O)—O—$R^9$—Si($R^3R^4R^5$) group in which $R^9$ is an alkylene group with 1 to 6 carbon atoms; and $R^3$, $R^4$, and $R^5$ each independently are an unbranched or branched alkyl group with 1 to 6 carbon atoms or an aryl group.

A compound of general formula I may be provided in which

A is selected from the group consisting of an —$R^1$—O—$R^2$ group, an —$R^1$—Si($R^3R^4R^5$) group, an —$R^1$—O—Si($R^3R^4R^5$) group, a —C(O)—O—$R^9$—Si($R^3R^4R^5$) group, a —CH(O—$R^6$)(O—$R^7$) group, an —$R^1$—CH (O—$R^6$)(O—$R^7$) group, an —$R^1$—O—C(O)—O—$R^8$ group;

SG is a protective group;

$R^1$ is a divalent hydrocarbon residue with 1 to 12 carbon atoms;

$R^2$ is a monovalent hydrocarbon residue with 1 to 12 carbon atoms;

$R^3$, $R^4$, and $R^5$ each independently are a monovalent hydrocarbon residue with 1 to 12 carbon atoms;

$R^6$ and $R^7$ each independently are a monovalent hydrocarbon residue with 1 to 12 carbon atoms;

$R^8$ is a monovalent hydrocarbon residue with 1 to 12 carbon atoms; and $R^9$ is a divalent hydrocarbon residue with 1 to 12 carbon atoms.

It may further be provided that the entity A is selected from the group consisting of an —$R^1$—O—$R^2$ group in which $R^1$ is an alkylene group with 1 to 6 carbon atoms; and $R^2$ is an unbranched or branched alkyl group with 1 to 6 carbon atoms;

an —$R^1$—Si($R^3R^4R^5$) group in which $R^1$ is an alkylene group with 1 to 6 carbon atoms; and $R^3$, $R^4$, and $R^5$ each independently are an unbranched or branched alkyl group with 1 to 6 carbon atoms or an aryl group; and a —C(O)—O—$R^9$—Si($R^3R^4R^5$) group in which $R^9$ is an alkylene group with 1 to 6 carbon atoms; and $R^3$, $R^4$, and $R^5$ each independently are an unbranched or branched alkyl group with 1 to 6 carbon atoms or an aryl group.

Preferred examples of a compound of general formula Ia-A are:

(i) 2-((((9H-fluoren-9-yl)methoxy)carbonyl)amino)-3-(3-iodo-4-(methoxymethoxy)phenyl)propionic acid, also referred to as Fmoc-D/L-Tyr(MOM)-OH, wherein Fmoc-D-Tyr(MOM)-OH is particularly preferred;

(ii) 2-((((9H-fluoren-9-yl)methoxy)carbonyl)amino)-3-(3-iodo-4-(((2-(trimethylsilyl)ethoxy)carbonyl)oxy) phenyl)propionic acid, also referred to as Fmoc-D/L-Tyr(TEOC)-OH, wherein Fmoc-D-Tyr(TEOC)-OH is particularly preferred;

(iii) 2-((((9H-fluoren-9-yl)methoxy)carbonyl)amino)-3-(4-(2-(tert-butyldiphenylsilyl)ethoxy)-3-iodophenyl) propionic acid, also referred to as Fmoc-D/L-Tyr (TBDPSE)-OH, wherein Fmoc-D-Tyr(TBDPSE)-OH is particularly preferred; and (iv) 2-((((9H-fluoren-9-yemethoxy)carbonyl)amino)-3-(4-(tert-butoxy)-3-iodo-phenyl)propionic acid, also referred to as Fmoc-D/L-Tyr(tBu)-OH, wherein Fmoc-D-Tyr(tBu)-OH is particularly preferred.

Preferred examples of a compound of general formula Ib-A are:

(i) 2-((tert-butoxycarbonyl)amino)-3-(3-iodo-4-(methoxymethoxy)phenyl)propionic acid, also referred to as boc-D/L-Tyr(MOM)-OH, wherein boc-D-Tyr (MOM)-OH is preferred;

(ii) 2-((tert-butoxycarbonyl)amino)-3-(3-iodo-4-(((2-(trimethylsilyl)ethoxy)carbonyl)oxy)phenyl)propionic acid, also referred to as boc-D/L-Tyr(TEOC)-OH, wherein boc-D-Tyr(TEOC)-OH is preferred;

(iii) 2-((tert-butoxycarbonyl)amino)-3-(4-(2-(tert-butyldiphenylsilyl)ethoxy)-3-iodophenyl)propionic acid, also referred to as boc-D/L-Tyr(TBDPSE)-OH, wherein boc-D-Tyr(TBDPSE)-OH is preferred; and (iv) 2-((tert-butoxycarbonyl)amino)-3-(4-(tert-butoxy)-3-iodophenyl)propionic acid, also referred to as boc-D/L-Tyr(tBu)-OH, wherein boc-D-Tyr(tBu)-OH is preferred.

In accordance with the invention further provided is a method for the preparation of the compound of general formula I according to the invention. For that, a compound of general formula II (formula II)

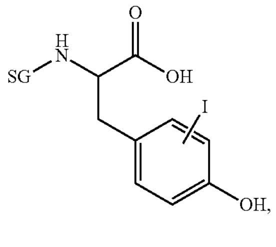

wherein SG has the meanings given in connection with general formula I, is reacted with a compound of general formula X-A, wherein X is halogen or ammonium and A has the meanings given in connection with general formula I, to a compound of general formula I (formula I)

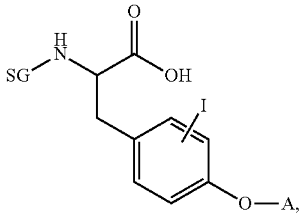

wherein SG and A have the meanings given in connection with formula I. Protective group A is introduced into the compound X-A by means of the compound of general formula II. If in the compound of general formula II SG is Fmoc, so said compound is Fmoc-iodo-D/L-tyrosine, systematically referred to as 2-((((9H-fluoren-9-yl)methoxy)carbonyl)amino)-3-(4-hydroxy-iodophenyl)propionic acid. Preferably, the compound of general formula II is Fmoc-iodo-D-tyrosine. If in the compound of general formula II SG is boc, so said compound is boc-iodo-D/L-tyrosine, systematically referred to as 2-((tert-butoxycarbonyl)amino)-3-(4-hydroxy-iodophenyl)propionic acid, wherein boc-iodo-D-tyrosine is preferred.

A particularly preferred compound of general formula II is Fmoc-3-iodo-D/L-tyrosine, systematically referred to as 2-((((9H-fluoren-9-yl)methoxy)carbonyl)amino)-3-(4-hydroxy-3-iodophenyl)propionic acid. In said compound the phenolic iodine atom is in the 3 position. Particularly preferred is Fmoc-3-iodo-D-tyrosine. A further preferred compound of general formula II is boc-3-iodo-D/L-tyrosine, systematically referred to as 2-((tert-butoxycarbonyl)amino)-3-(4-hydroxy-3-iodophenyl)propionic acid. In said compound the phenolic iodine atom is in the 3 position. Particularly preferred is boc-3-iodo-D-tyrosine.

The compound of general formula II can be prepared from a compound of general formula IV (formula IV)

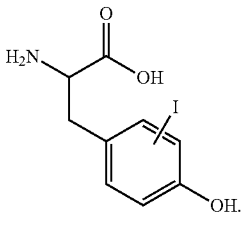

The amine function of the compound of general formula IV is protected by the introduction of a protective group SG. For that, the compound of general formula IV for example can be reacted with a 9-fluorenylmethoxycarbonyl reagent or a tert-butoxycarbonyl reagent. The 9-fluorenylmethoxycarbonyl compound can be for example (9-fluorenylmethoxycarbonyloxy)-succinimide (Fmoc-OSu). The tert-butoxycarbonyl reagent can be for example di-tert-butyldicarbonate ($Boc_2O$). The compound of general formula IV is D/L-iodotyrosine, wherein D-iodotyrosine is preferred.

It may be provided that the compound of general formula II is reacted with a compound of general formula X-A to obtain a compound of general formula III (formula III)

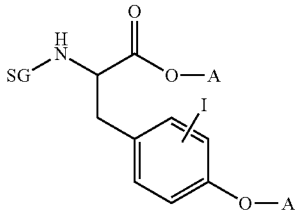

and the compound of general formula III is subsequently reacted to a compound of general formula I. Scheme 1 illustrates the inventive preparation of an inventive compound of general formula I from a compound of general formula II.

scheme 1

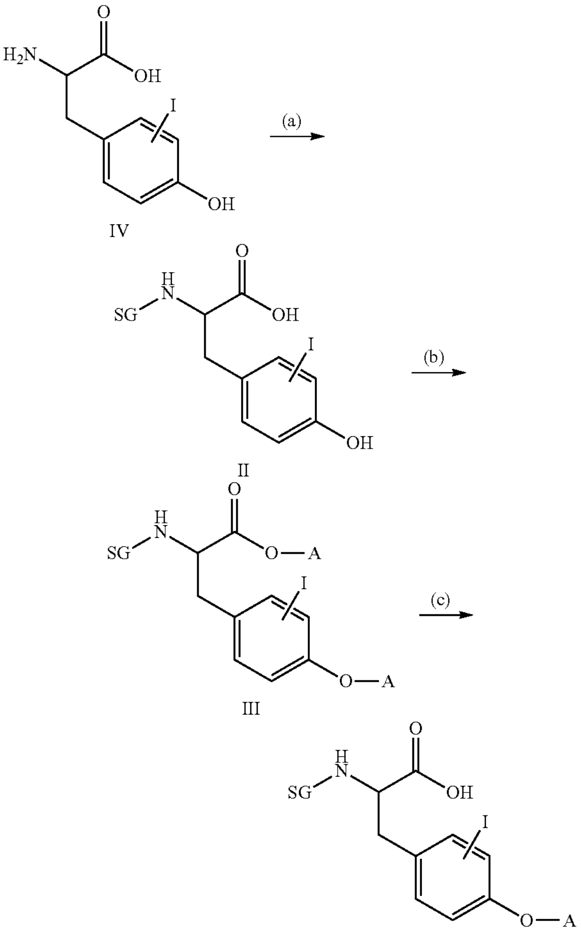

IV

II

III

I

Scheme 1a illustrates the inventive preparation of an inventive compound of general formula Ia from a compound of general formula IIa. Compound IIa is a compound of general formula II in which SG is Fmoc. The method shown in scheme 1a is one embodiment of the method shown in scheme 1.

scheme 1a

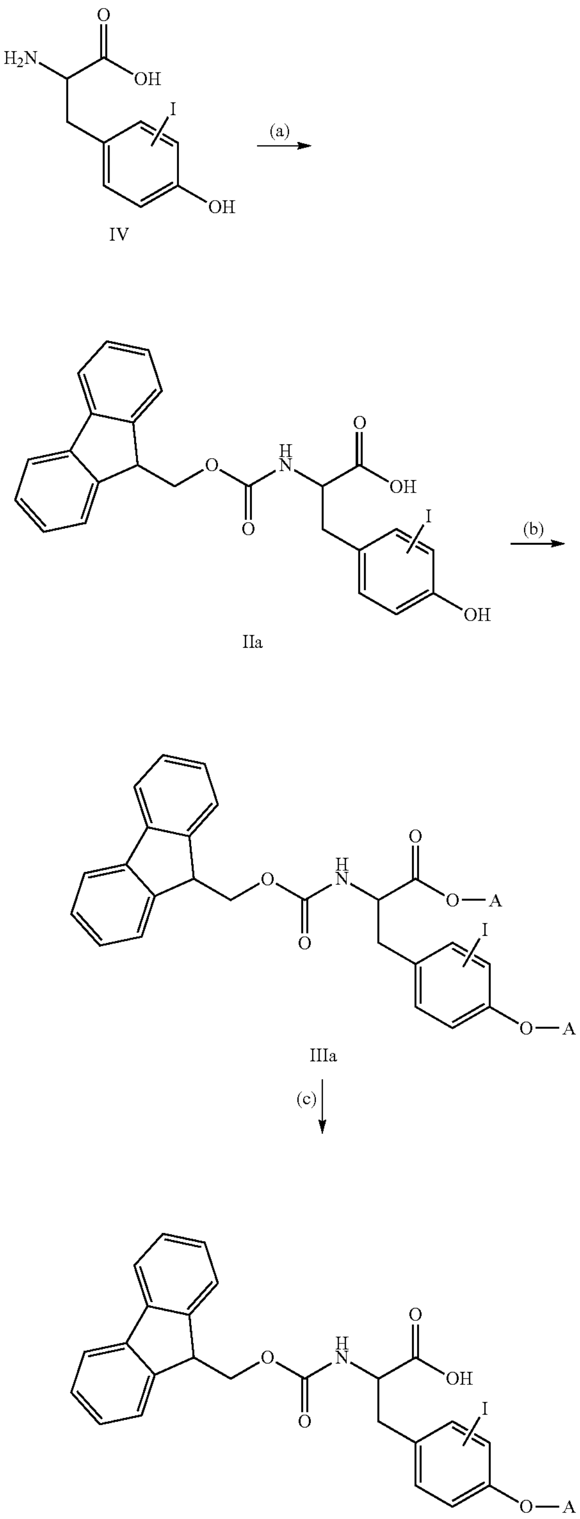

IV
IIa
IIIa
Ia

Scheme 2 illustrates the inventive preparation of an inventive compound of general formula Ia-A from 3-iodo-D/L-tyrosine. The method shown in scheme 2 is one embodiment of the method shown in scheme 1a.

scheme 2

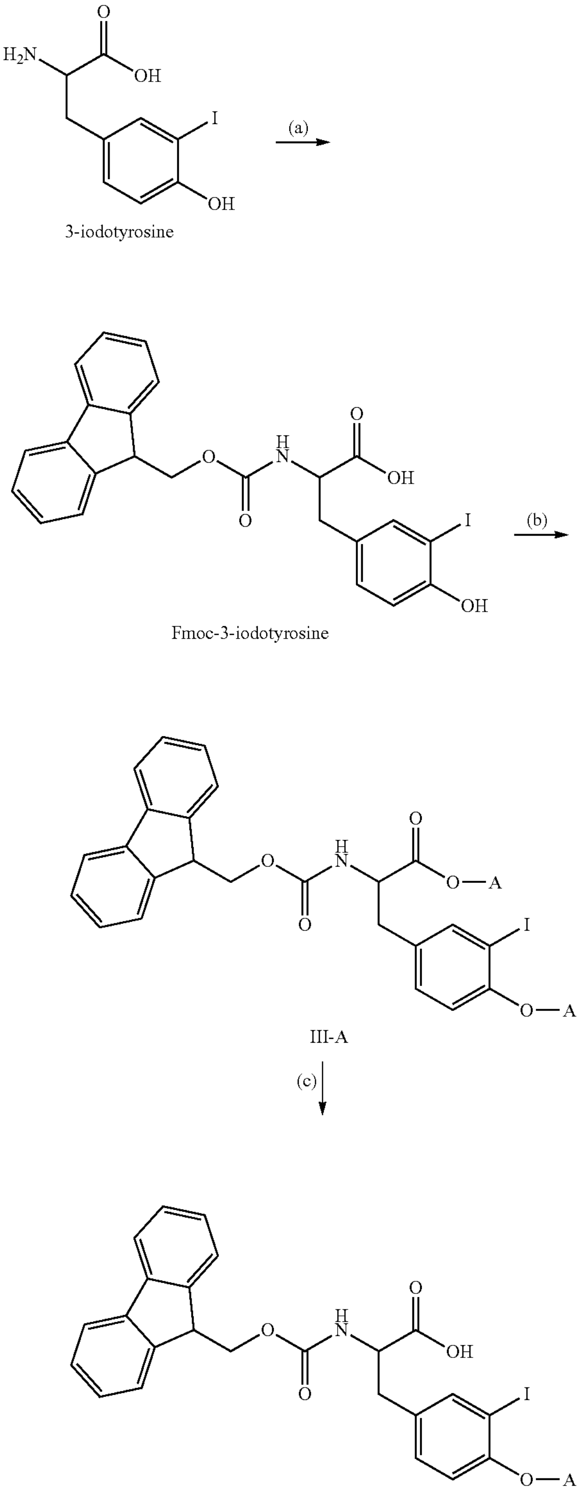

3-iodotyrosine
Fmoc-3-iodotyrosine
III-A
I-A

Step (a) of the method shown in scheme 1 provides the reaction of a compound of general formula IV to a compound of general formula II. Here, a protective group to protect the amine function is introduced at the N-terminus of the compound of general formula IV. For that, the compound of general formula IV can be reacted for example with (9-fluorenylmethoxycarbonyloxy)-succinimide (Fmoc-OSu) (see scheme 1a) or di-tert-butyldicarbonate ($Boc_2O$). The compound of general formula II corresponds to the compound of general formula IV, except that the N-terminus of the compound of general formula IV is protected by a protective group SG. Ambient temperature means a temperature in the range of 18 to 25° C.

If in step (a) of scheme 1 Fmoc is to be introduced as the protective group SG, so step (a) can be carried out at ambient pressure and ambient temperature under a protective gas, for example under argon atmosphere. In this case, to introduce Fmoc as the protective group SG step (a) is preferably carried out in a mixture of an aqueous sodium carbonate solution and 1,4-dioxane.

If in step (a) of scheme 1 boc is to be introduced as the protective group SG, so step (a) can be carried out at ambient pressure and ambient temperature in air. A protective gas is not required. In this case, step (a) is preferably carried out in a mixture of water, tetrahydrofuran, and triethylamine.

Step (b) of the method shown in scheme 1 provides the reaction of a compound of general formula II to a compound of general formula III. Here, the hydroxy group at the C-terminus of the compound of general formula II and the phenolic hydroxy group are protected by an entity A. For that, the compound of general formula II is reacted with the compound X-A. The reaction can take place in an aprotic solvent such as dichloromethane (DCM) in the presence of an auxiliary base such as diisopropylethylamine (Hunig base, DIPEA) and a phase transfer catalyst such as tetrabutylammoniumchloride (TBAC1). The reaction can be carried out in a temperature range between 0° C. and ambient temperature. It can be carried out at ambient pressure and under a protective gas, for example under argon atmosphere. The compound of general formula II corresponds to the compound of general formula II, except that the hydroxy group at the C-terminus of the compound of general formula II and the phenolic hydroxy group are protected by the entity A.

Step (c) of the method shown in scheme 1 provides the reaction of a compound of general formula III to a compound of general formula I. Here, the entity A protecting the hydroxy group at the C-terminus of the compound of general formula III is cleaved off, while the entity A protecting the phenolic hydroxy group remains. Cleavage takes place in the basic range, for example in a pyridine/water mixture. The reaction can be carried out in a temperature range between 0° C. and ambient temperature. It can be carried out at ambient pressure. A protective gas is not required. The compound of general formula I corresponds to the compound of general formula III, except that there is a hydroxy group at the C-terminus of the compound of general formula I.

Further details on the method according to the invention have already been described in connection with the compound of general formula I according to the invention. Reference is made to their description.

In accordance with the invention provided is a use of a compound of general formula I according to the invention for the preparation of a peptide. The peptide prepared has at least one iodotyrosine entity. The peptide prepared can correspond to known peptides, apart from the fact that at least one, preferably exactly one tyrosine entity is replaced by a 3-iodotyrosine entity. The 3-iodotyrosine entity can be prepared by reacting a compound of general formula I with an amino acid or an amino acid sequence to obtain a peptide. Preparation of the peptide can be done by means of synthesis methods known per se, for example by means of the Merrifield synthesis. One way for peptide synthesis is described in Robert Bruce Merrifield, Solid phase peptide synthesis Journal of the American Chemical Society, Volume 85, Number 14, pp. 2149-2154. After having prepared the peptide entity A derived from the compound of general formula I is cleaved off which gives a peptide with a 3-iodotyrosine entity the phenolic OH group of which is unprotected.

Scheme 3 illustrates the preparation of a peptide of general formula V, which has an iodotyrosine entity, using a compound of general formula I.

scheme 3

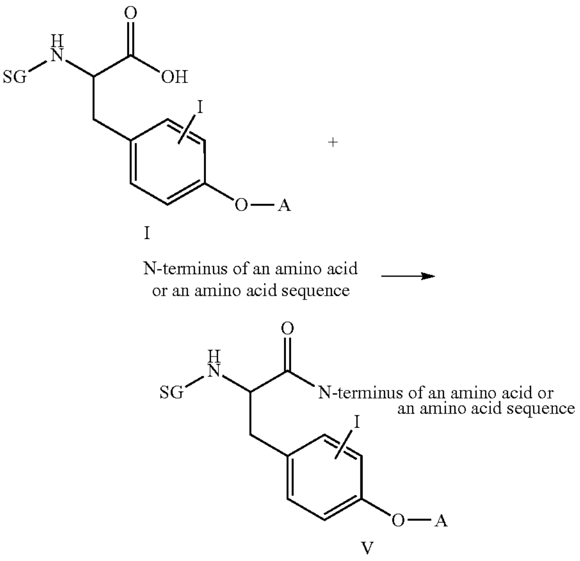

I

V

Scheme 3a illustrates the preparation of a peptide of general formula Va, which has an iodotyrosine entity, using a compound of general formula Ia. A peptide of general formula Va is a peptide of general formula V in which SG is Fmoc.

scheme 3a

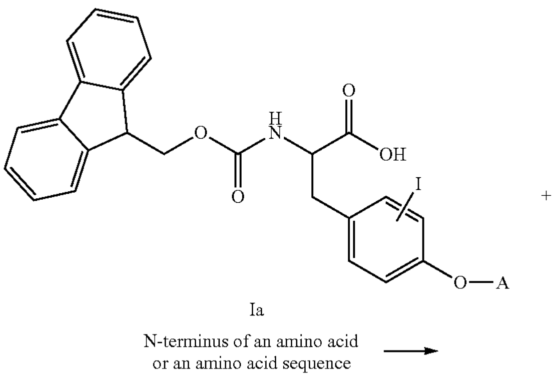

Ia

-continued

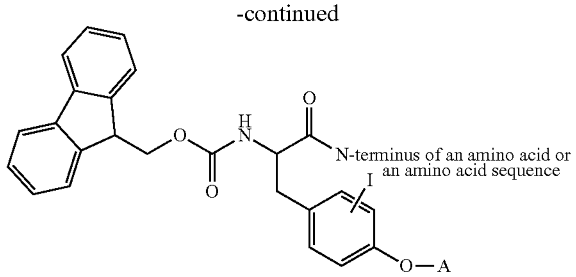

Va

Subsequently, the protective group SG can be cleaved off, thereby converting the compound of general formula V to a compound of general formula VI, as is shown in scheme 4 and scheme 4a.

scheme 4

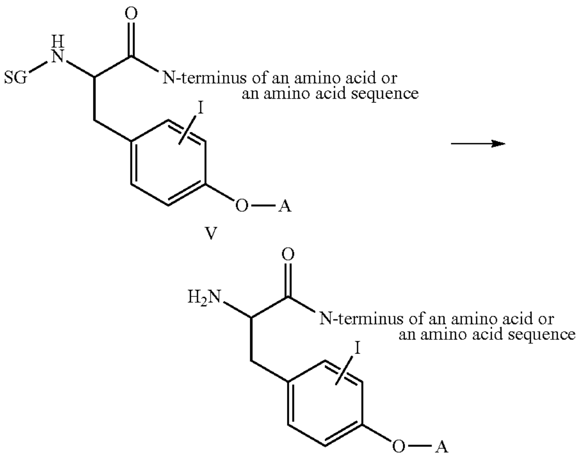

V

VI scheme 4a

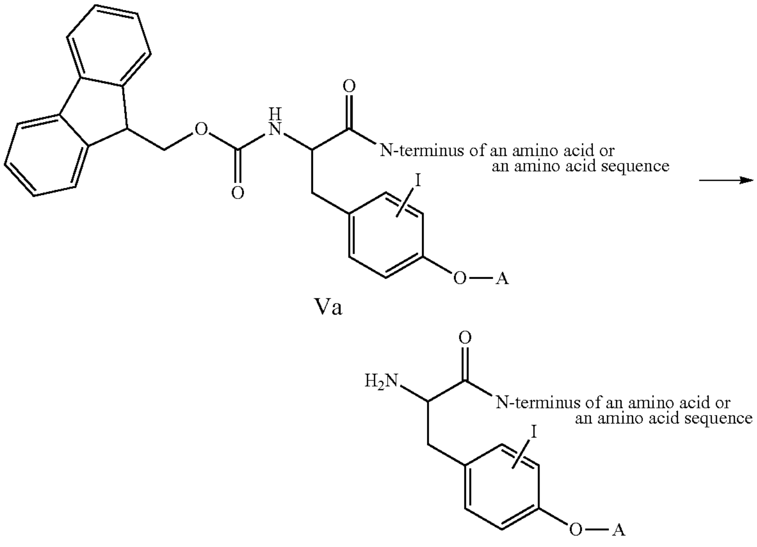

Va

VI

If the iodotyrosine entity shall not be a terminal entity of the peptide, so a further amino acid can be coupled to the N-terminus of the compound of general formula VI, thereby obtaining a compound of general formula VII, as is shown in scheme 5.

scheme 5

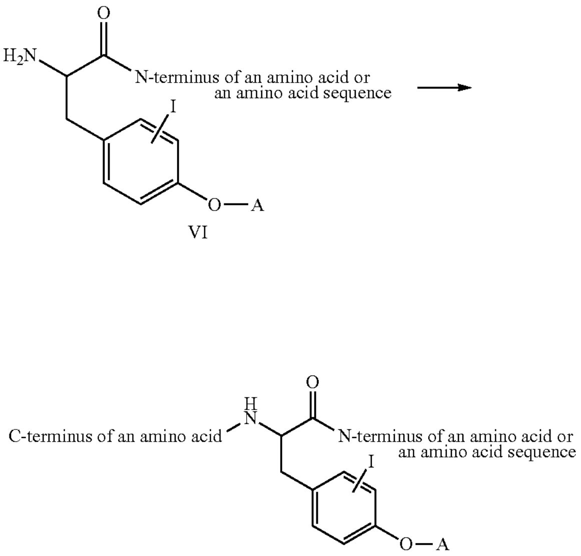

VI

VII

One or more additional amino acids can be bound to the further amino acid whereby a peptide of general formula VIII

VIII

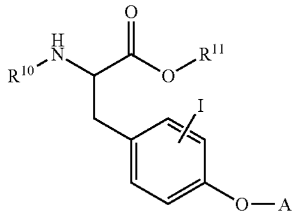

can be obtained in which A has the meanings given in connection with the compound of general formula I, $R^{10}$ is hydrogen or one or more amino acid entities; and $R^{11}$ is hydrogen or one or more amino acid entities, with the proviso that if $R^{10}$ is hydrogen, $R^{11}$ is not hydrogen; and that if $R^{11}$ is hydrogen, $R^{10}$ is not hydrogen. An amino acid entity may be an entity which has an NH group or an $NR^{12}$ group at the N-terminus, wherein $R^{12}$ is a methyl group.

The compound of general formula VIII can be converted to a peptide of general formula IX by cleaving off the entity A, as is shown in scheme 6.

scheme 6

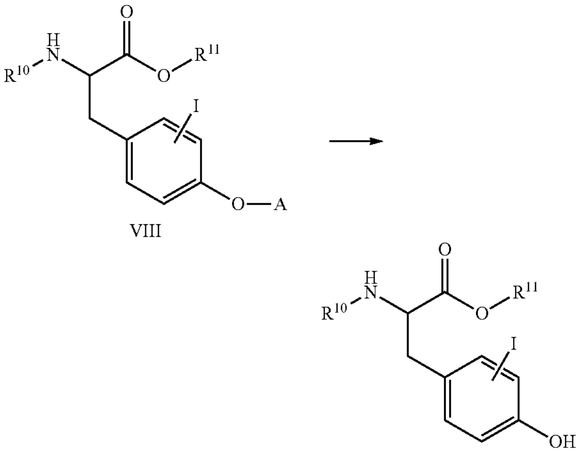

VIII

IX

Cleavage of entity A is done in the acidic range, for example in the course of the total deprotection of the peptide. For the total deprotection of the peptide preferably an aqueous solution of trifluoroacetic acid (TFA), for example a 95% TFA solution is used. The reaction can be carried out in a temperature range between 0° C. and ambient temperature. It can be carried out at ambient pressure. A protective gas is not required. The compound of general formula IX corresponds to the compound of general formula VIII, except that entity A was cleaved off to obtain a hydroxy group.

The term "alkyl", unless otherwise stated, in particular refers to a monovalent saturated aliphatic hydrocarbon group with a branched or unbranched carbon chain with 1 to 12 carbon atoms, preferably 1 to 8 carbon atoms and particularly preferred 1 to 6 carbon atoms. Examples of alkyl groups comprise, but are not limited to, methyl, ethyl, propyl, isopropyl, isobutyl, sec-butyl, tert-butyl, pentyl, n-hexyl, octyl, dodecyl, and the like.

The term "alkylene", unless otherwise stated, in particular refers to a divalent saturated aliphatic hydrocarbon group with a branched or unbranched carbon chain with 1 to 12 carbon atoms, preferably 1 to 8 carbon atoms and particularly preferred 1 to 6 carbon atoms. Examples of alkylene groups comprise, but are not limited to, methylene, ethylene, propylene, butylene and the like.

The term "aryl", unless otherwise stated, refers to a cyclic, aromatic hydrocarbon group consisting of a mono-, bi- or tricyclic aromatic ring system with 5 to 18 ring atoms, preferably 5 or 6 ring atoms. Examples of aryl groups comprise, but are not limited to, phenyl, naphthyl, anthracenyl, phenanthryl, fluorenyl, indenyl, azulenyl, biphenyl, methylenediphenyl and the like, including partially hydrogenated derivatives thereof. The aryl group, unless otherwise stated, can be mono or multivalent, for example mono or divalent.

DETAILED DESCRIPTION

In the following, the invention is explained in more detail with the help of examples which are not intended to limit the invention.

Examples of inventive compounds are given in table 1. The compounds 1D, 2D, 3D, and 4D possess am R configuration and are derivatives of D-tyrosine. The compounds 1L, 2L, 3L, and 4L possess an S configuration and are derivatives of L-tyrosine.

TABLE 1

| Compound | Structure | Name (abbr. chem. name) |
| --- | --- | --- |
| 1D | 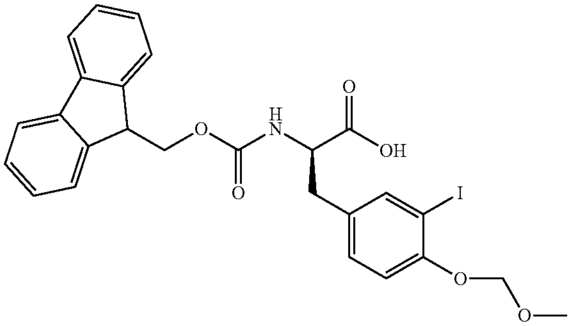 [SMILES: COCOc1ccc(C[C@@H](NC(=O)OCC2c3ccccc3-c3ccccc32)C(=O)O)cc1I] | (R)-2-((((9H-fluoren-9-yl)methoxy)carbonyl)amino)-3-(3-iodo-4-(methoxymethoxy)phenyl) propionic acid (Fmoc-3-iodo-D-Tyr(MOM)-OH)) |

TABLE 1-continued

| Compound | Structure | Name (abbr. chem. name) |
|---|---|---|
| 1L | 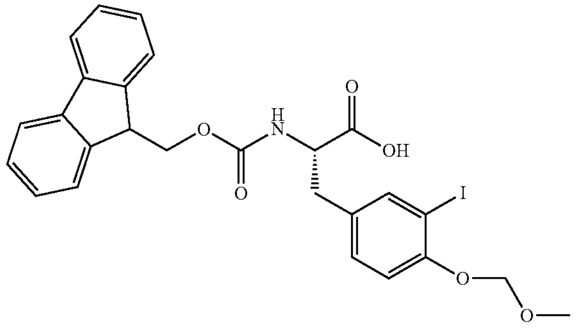 [SMILES: COCOc1ccc(C[C@H](NC(=O)OCC2c3ccccc3-c3ccccc32)C(=O)O)cc1I] | (S)-2-((((9H-fluoren-9-yl)methoxy) carbonyl)amino)-3-(3-iodo-4-(methoxymethoxy)phenyl) propionic acid (Fmoc-3-iodo-L-Tyr(MOM)-OH)) |
| 2D | 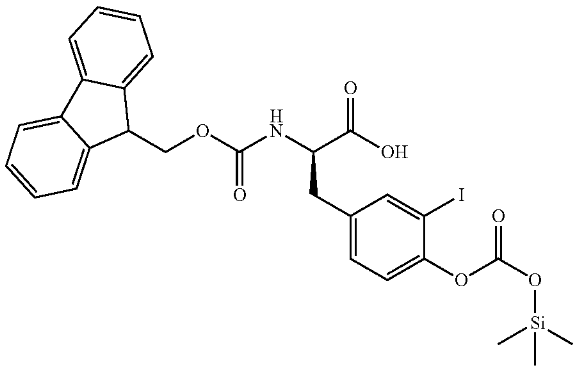 [SMILES: C[Si](C)(C)OC(=O)Oc1ccc(C[C@@H](NC(=O)OCC2c3ccccc3-c3ccccc32)C(=O)O)cc1I] | (R)-2-((((9H-Fluoren-9-yl)methoxy) carbonyl)amino)-3-(3-iodo-4-(((2-(trimethylsilyl)ethoxy) carbonyl)oxy)phenyl)propionic acid (Fmoc-3-iodo-D-Tyr(TEOC)-OH) |
| 2L | 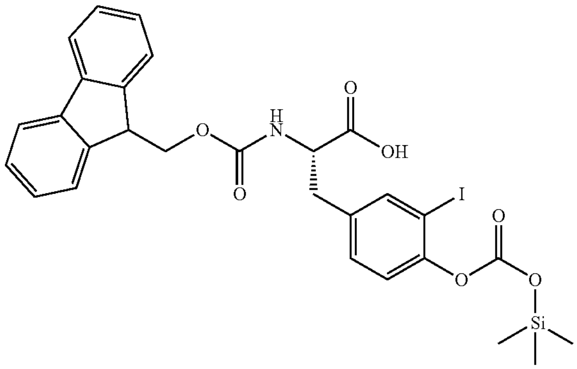 [SMILES: C[Si](C)(C)OC(=O)Oc1ccc(C[C@H](NC(=O)OCC2c3ccccc3-c3ccccc32)C(=O)O)cc1I] | (S)-2-((((9H-fluoren-9-yl)methoxy) carbonyl)amino)-3-(3-iodo-4-(((2-(trimethylsilyl)ethoxy) carbonyl)oxy)phenyl)propionic acid (Fmoc-3-iodo-L-Tyr(TEOC)-OH) |
| 3D | 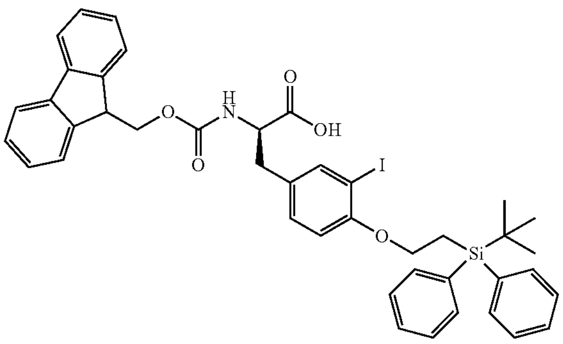 [SMILES: CC(C)(C)[Si](CCOc1ccc(C[C@@H](NC(=O)OCC2c3ccccc3-c3ccccc32)C(=O)O)cc1I)(c1ccccc1)c1ccccc1] | (R)-2-((((9H-fluoren-9-yl)methoxy) carbonyl)amino)-3-(4-(2-(tert-butyldiphenylsilyl)ethoxy)-3-iodophenyl)propionic acid (Fmoc-3-iodo-D-Tyr(TBDPSE)-OH) |

TABLE 1-continued

| Compound | Structure | Name (abbr. chem. name) |
|---|---|---|
| 3L | 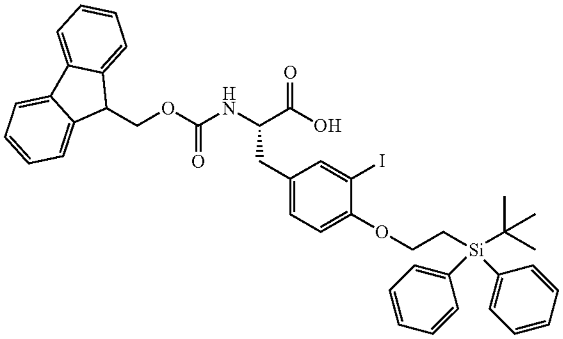 [SMILES: CC(C)(C)[Si](CCOc1ccc(C[C@H](NC(=O)OCC2c3ccccc3-c3ccccc32)C(=O)O)cc1I)(c1ccccc1)c1ccccc1] | (S)-2-((((9H-fluoren-9-yl) methoxy)carbonyl)amino)-3-(4-(2-(tert-butyldiphenylsilyl)ethoxy)-3-iodophenyl)propionic acid (Fmoc-3-iodo-L-Tyr(TBDPSE)-OH) |
| 4D | 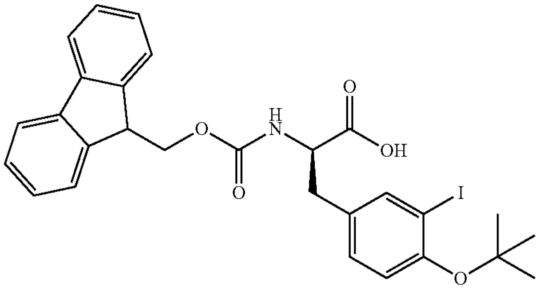 [SMILES: CC(C)(C)Oc1ccc(C[C@@H](NC(=O)OCC2c3ccccc3-c3ccccc32)C(=O)O)cc1I] | (R)-2-((((9H-fluoren-9-yl)methoxy) carbonyl)amino)-3-(4-(tert-butoxy)-3-iodophenyl)propionic acid (Fmoc-3-iodo-D-Tyr(tBu)-OH) |
| 4L | 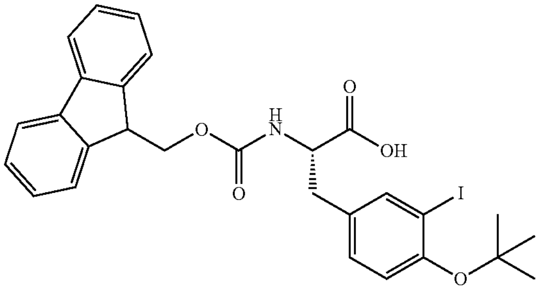 [SMILES: CC(C)(C)Oc1ccc(C[C@H](NC(=O)OCC2c3ccccc3-c3ccccc32)C(=O)O)cc1I] | (S)-2-((((9H-fluoren-9-yl)methoxy) carbonyl)amino)-3-(4-(tert-butoxy)-3-iodophenyl)propionic acid (Fmoc-3-iodo-L-Tyr(tBu)-OH) |

The compounds mentioned in table 1 are exemplary compounds of general formula I and of general formula Ia. The compounds 1D and 1L are compounds of general formula Ia in which A is an —$R^1$—O—$R^2$ group in which $R^1$ is a methylene group and $R^2$ is a methyl group. The compounds 2D and 2L are compounds of general formula Ia in which A is an —$R^1$—Si($R^3R^4R^5$) group in which $R^1$ is —$CH_2$—$CH_2$— and $R^3$, $R^4$ and $R^5$ each are a methyl group. The compounds 3D and 3L are compounds of general formula Ia in which A is an —$R^1$—Si($R^3R^4R^5$) group in which $R^1$ is —$CH_2$—$CH_2$—$CH_2$—, $R^3$ and $R^4$ each are a phenyl group and $R^5$ is a tert-butyl group. The compounds 4D and 4L are compounds of general formula Ia in which A is a tert-butyl group.

Further examples of inventive compounds are given in table 1 a. The compounds 5D, 6D, 7D and 8D possess an R configuration and are derivatives of D-tyrosine. The compounds 5L, 6L, 7L and 8L possess an S configuration and are derivatives of L-tyrosine.

TABLE 1a

| Compound | Structure | Name (abbr. chem. name) |
|---|---|---|
| 5D | 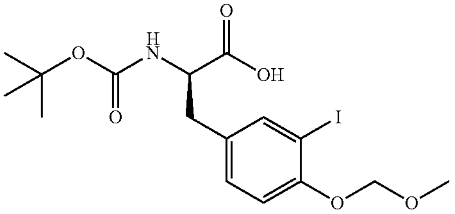 [SMILES: COCOc1ccc(C[C@@H](NC(=O)OC(C)(C)C)C(=O)O)cc1I] | (R)-2-((tert-butoxycarbonyl) amino)-3-(3-iodo-4-(methoxymethoxy) phenyl)propionic acid (boc-3-iodo-D-Tyr(MOM)-OH)) |

TABLE 1a-continued

| Compound | Structure | Name (abbr. chem. name) |
|---|---|---|
| 5L | 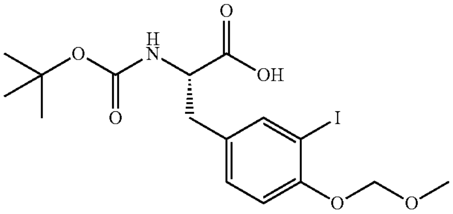 [SMILES: COCOc1ccc(C[C@H](NC(=O)OC(C)(C)C)C(=O)O)cc1I] | (S)-2-((tert-butoxycar-bonyl)amino)-3-(3-iodo-4-(methoxymethoxy) phenyl)propionic acid (boc-3-iodo-L-Tyr(MOM)-OH)) |
| 6D | 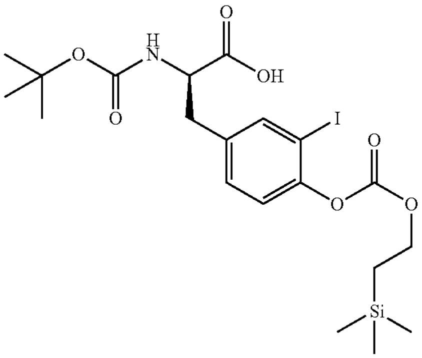 [SMILES: CC(C)(C)OC(=O)N[C@H](Cc1ccc(OC(=O)OCC[Si](C)(C)C)c(I)c1)C(=O)O] | (R)-2-((tert-butoxycarbonyl) amino)-3-(3-iodo-4-(((2-(trimethylsilyl) ethoxy)carbonyl)oxy) phenyl)propionic acid (boc-3-iodo-D-Tyr(TEOC)-OH) |
| 6L | 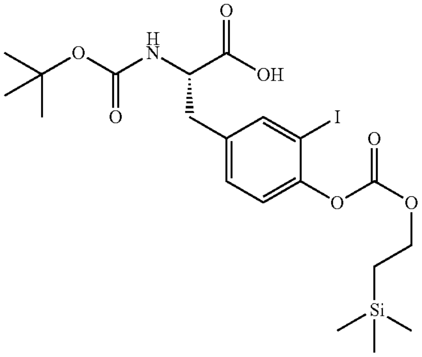 [SMILES: CC(C)(C)OC(=O)N[C@@H](Cc1ccc(OC(=O)OCC[Si](C)(C)C)c(I)c1)C(=O)O] | (S)-2-((tert-butoxycarbonyl)amino)-3-(3-iodo-4-(((2-(trimethylsilyl) ethoxy)carbonyl)oxy) phenyl)propionic acid (boc-3-iodo-L-Tyr(TEOC)-OH) |
| 7D | 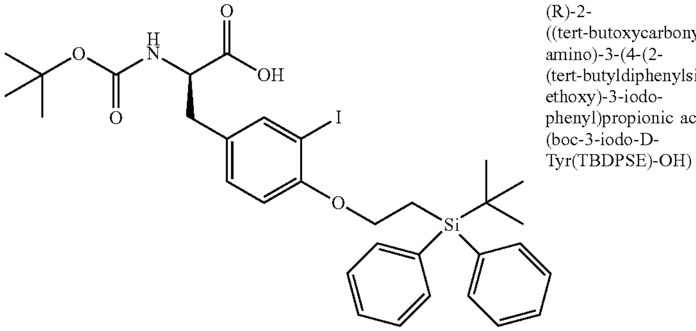 | (R)-2-((tert-butoxycarbonyl) amino)-3-(4-(2-(tert-butyldiphenylsilyl) ethoxy)-3-iodo-phenyl)propionic acid (boc-3-iodo-D-Tyr(TBDPSE)-OH) |

TABLE 1a-continued

| Compound | Structure | Name (abbr. chem. name) |
|---|---|---|
| 7L | 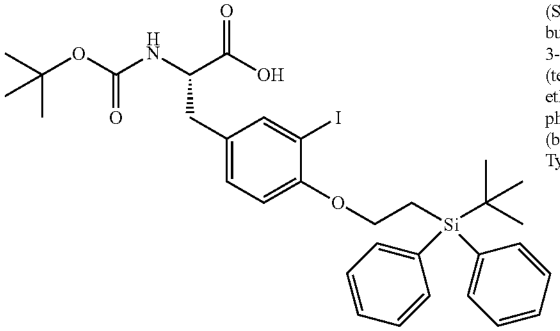 | (S)-2-((tert-butoxycar-bonyl)amino)-3-(4-(2-(tert-butyldiphenylsilyl) ethoxy)-3-iodo-phenyl)propionic acid (boc-3-iodo-L-Tyr(TBDPSE)-OH) |
| 8D | 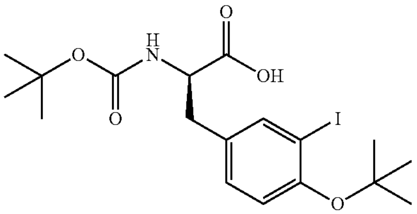 [SMILES: CC(C)(C)OC(=O)N[C@H](Cc1ccc(OC(C)(C)C)c(I)c1)C(=O)O] | (R)-2-((tert-butoxycarbonyl) amino)-3-(4-(tert-butoxy)-3-iodo-phenyl)propionic acid (boc-3-iodo-D-Tyr(tBu)-OH) |
| 8L | 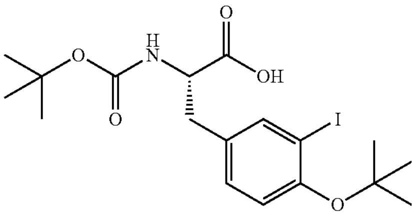 [SMILES: CC(C)(C)OC(=O)N[C@@H](Cc1ccc(OC(C)(C)C)c(I)c1)C(=O)O] | (S)-2-((tert-butoxycarbonyl) amino)-3-(4-(tert-butoxy)-3-iodo-phenyl)propionic acid (boc-3-iodo-L-Tyr(tBu)-OH) |

The compounds mentioned in table 1a are exemplary compounds of general formula I and of general formula Ib. The compounds 5D and 5L are compounds of general formula Ib in which A is an —$R^1$—O—$R^2$ group in which $R^1$ is a methylene group and $R^2$ is a methyl group. The compounds 6D and 6L are compounds of general formula Ib in which A is an —$R^1$—Si($R^3R^4R^5$) group in which $R^1$ is —$CH_2$—$CH_2$— and $R^3$, $R^4$ and $R^5$ each are a methyl group. The compounds 7D and 7L are compounds of general formula Ib in which A is an —$R^1$—Si($R^3R^4R^5$) group in which $R^1$ is —$CH_2$—$CH_2$—$CH_2$—, $R^3$ and $R^4$ each are a phenyl group and $R^5$ is a tert-butyl group. The compounds 8D and 8L are compounds of general formula Ib in which A is a tert-butyl group.

The abbreviations used in the abbreviated chemical names have the following meaning:

Boc tert-butoxy carbonyl
Fmoc 9-fluorenylmethyloxycarbonyl
MOM methoxymethyl
OH hydroxy group of the carboxyl entity
TBDPSE tert-butyldiphenylsilylethyl
TEOC 2-(trimethylsilyl)ethoxycarbonyl
D-Tyr D-tyrosine
L-Tyr L-tyrosine Example 1

Synthesis of Fmoc-3-iodo-D-Tyr(MOM)-OH (1D)

The synthesis of Fmoc-3-iodo-D-Tyr(MOM)-OH was carried out as described in scheme B1:

scheme B1

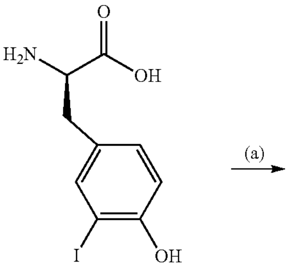

11

-continued

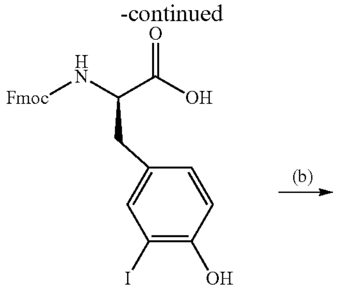

12

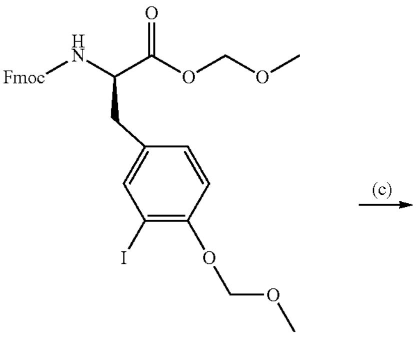

13

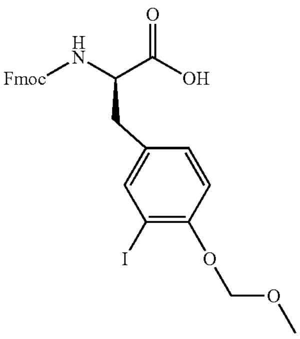

1D

In step (a) (R)-2-amino-3-(4-hydroxy-3-iodophenyl)propionic acid 11 (also referred to as 3-iodo-D-tyrosine or 3-iodo-D-Tyr-OH) is reacted with N-(9-fluorenylmethoxycarbonyloxy)-succinimide (Fmoc-OSu) to obtain (R)-2-((((9H-fluoren-9-yl)methoxy)carbonyl)amino)-3-(4-hydroxy-3-iodophenyl)propionic acid 12 (also referred to as Fmoc-3-iodo-D-Tyr-OH). The reaction takes place in mixture of an aqueous sodium carbonate solution and 1,4-dioxane. Then, in step (b) compound 12 is reacted with methoxymethylbromide ($CH_3$—O—$CH_2$—Br) to methoxymethyl-(R)-2-((((9H-fluoren-9-yl)methoxy)carbonyl)amino)-3-(3-iodo-4-(methoxymethoxy)phenyl)propanoate 13 (also referred to as Fmoc-3-iodo-D-Tyr(MOM)-OMOM). The reaction takes place in dichloromethane (DCM) in the presence of diisopropylethylamine (DIPEA) and tetrabutylammoniumchloride (TBACl). Then, in step (c) compound 13 is reacted to the target compound 1D. The reaction is done in a mixture of tetrahydrofuran (THF), water and pyridine.

Analysis of the compound prepared was done both by HPLC analysis and LC-MS analysis.

a) Synthesis of Fmoc-3-iodo-D-Tyr-OH (12)

3-Iodo-D-Tyr-OH 11 (5 g, 16.28 mmol) was suspended in 50 ml of an aqueous $Na_2CO_3$ solution (1.726 g, 16.28 mmol) in an argon atmosphere. 10 ml of dioxane were added and the yellow solution was cooled in an ice water bath. Fmoc-OSu (5.492 g, 16.28 mmol) dissolved in 50 ml of 1,4-dioxane was added dropwise via a dropping funnel under an argon atmosphere. Upon addition the reaction mixture was stirred in an ice water bath for 1 hr, then at room temperature. After 17 hrs thin layer chromatography (TLC with (DCM/methanol (MeOH), 9:1 as the eluant) showed the complete conversion to the desired product Fmoc-3-iodo-D-Tyr-OH. 100 ml of $H_2O$ were added and the mixture was cooled in an ice water bath. 30% HCl (app. 4 ml) were added until a pH of 2 to 3 was reached. The mixture was extracted with ethyl acetate (3×150 ml), the combined organic phases were washed with $H_2O$ (2×150 ml) and saline (1×150 ml), dried over $Na_2SO_4$ and filtered (filter pore size 4). The solvent was removed by rotation evaporation, the residue was dried under high vacuum. Yield: 9.5 g (110%, quant.) of a white foamy solid. The crude product was used in the next step without any purification.

HPLC: $t_R$=7.26 min LC-MS: $t_R$=12.57 min, m/z=530.05 $[M+H]^+$, 1059.16 $[2M+H]^+$. $^1H$ NMR (DMSO-$d^6$, 500 MHz): 12.70 (br, 1H), 10.12 (s, 1H), 7.88 (m, 2H), 7.72-7.60 (m, 4H), 7.43-7.39 (m, 2H), 7.34-7.28 (m, 2H), 7.09 (m, 1H), 6.79 (m, 1H), 4.21-4.18 (m, 3H), 4.10-5.05 (m, 1H), 2.97-2.93 (m, 1H), 2.75-2.70 (m, 1H).

b) Synthesis of Fmoc-3-iodo-D-Tyr(MOM)-OMOM (13)

Fmoc-3-iodo-D-Tyr-OH 12 (9.5 g, i.e. 8.62 g, 16.28 mmol≡100%) was suspended in 120 ml of DCM (anhydrous) under an argon atmosphere. DIPEA (5.673 ml, 32.57 mmol, 2 eq.) was added, what after stirring for 10 min at room temperature resulted in a yellow solution. TBACl (453 mg, 1.628 mmol, 0.1 eq.) was added, and the mixture was cooled in an ice-cooled water bath. Methoxymethylbromide (MOMBr) (2.658 ml, 32.57 mmol, 2 eq.) diluted in 30 ml of DCM (anhydrous) was added dropwise via a dropping funnel under an argon atmosphere (gassing). After having completed the addition the reaction mixture was stirred with ice cooling. After one hour stirring was continued for further 18 hrs at room temperature. TLC (DCM/MeOH, 50:1) showed a complete conversion. 100 ml of $H_2O$ were added, and the mixture was vigorously stirred at room temperature. After 1 hr the phases were separated from each other in a separatory funnel. The aqueous phase was extracted several times each with 150 ml of DCM. The combined organic phases were washed with 1 N HCl (2×150 ml) and saline (150 ml), dried over $Na_2SO_4$ and filtered (filter pore size 4). The solvent was removed in vacuum; the remaining residue was dried in high vacuum. Yield: 11 g (109%, quant.) of a white foamy solid. The crude product was used in the next step without any purification.

HPLC: $t_R$=8.97 min LC-MS: $t_R$=14.76 min, m/z=618.12 $[M+H]^+$, 1235.32 $[2M+H]^+$.

c) Synthesis of Fmoc-3-iodo-D-Tyr(MOM)-OH (1D)

Fmoc-3-iodo-D-Tyr(MOM)-OMOM 13 was dissolved in 140 ml of THF (p.a.). During stirring a mixture of 400 ml of $H_2O$ and 10 ml of pyridine was added. Ca. 100 ml of THF (p.a.) were added until a clear mixture was obtained. The mixture was refluxed under vigorous stirring in an oil bath (70° C.). After 64 hrs HPLC (214 nm) showed a complete conversion of the starting material ($t_R$=8.96 min) to the product Fmoc-3-iodo-D-Tyr(MOM)-OH. The solvent (THF) was evaporated in vacuum. The mixture was laced with 2 N HCl (app. 120 ml) under ice cooling. The pH of the solution was between pH 4 and pH 5. The mixture was extracted with DCM (3×150 ml), the combined organic phases were washed with 0.5 N HCl (2×150 ml) and saturated saline (150 ml), dried over $Na_2SO_4$ and filtered. The solvent was evaporated in vacuum, the remaining residue was dried in high vacuum. Yield: 9.7 g (104%, quant.) of a white foamy solid. The crude product was purified by column chromatography (yield: 4.6 g, purity by HPLC (214 nm): >95%).

m/z=574.11 $[M+H]^+$, 1147.26 $[2M+H]^+$. $^1$H-NMR (400 MHz, $CDCl_3$) δ (ppm): 7.752 (d, 2H), 7.610 (s, 1H), 7.549 (m, 2H), 7.387 (t, 2H), 7.307 (m, 2H), 7.042 (d, 1H), 6.960 (d, 2H), 5.185 (s, 2H), 4.697 (m, 1H), 4.444 (m, 1H), 4.336 (m, 1H), 4.201 (m, 1H), 3.483 (s, 3H), 3.131 (m, 1H), 3.004 (m, 1H).

Example 2

Synthesis of boc-3-iodo-D-Tyr(MOM)-OH (5D)

The synthesis of boc-3-iodo-D-Tyr(MOM)-OH was carried out as described in scheme B2:

scheme B2

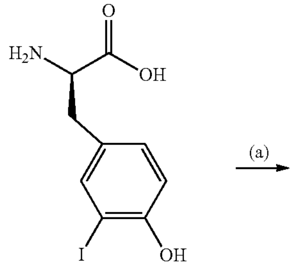

11

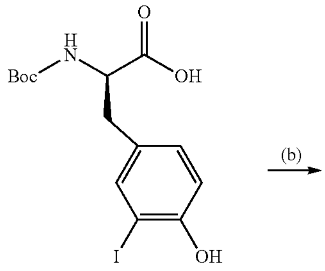

22

-continued

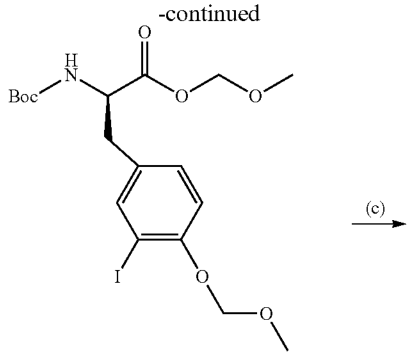

23

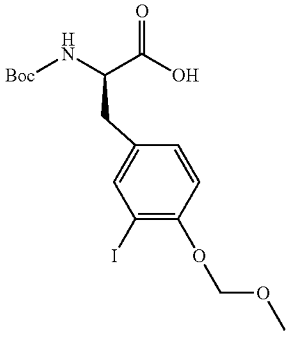

5D

In step (a) (R)-2-amino-3-(4-hydroxy-3-iodophenyl)propionic acid 11 (also referred to as 3-iodo-D-tyrosine or 3-iodo-D-Tyr-OH) was reacted with di-tert-butyldicarbonate ($Boc_2O$) to obtain (R)-2-((tert-butoxycarbonyl)amino)-3-(4-hydroxy-3-iodophenyl)propionic acid 22 (also referred to as boc-3-iodo-D-Tyr-OH). The reaction takes place in a mixture of water, tetrahydrofuran and triethylamine. Then, in step (b) compound 22 is reacted with methoxymethyl bromide ($CH_3$—O—$CH_2$—Br) to methoxymethyl-(R)-2-((tert-butoxycarbonyl)amino)-3-(3-iodo-4-(methoxymethoxy) phenyl)propanoate 23 (also referred to as boc-3-iodo-D-Tyr (MOM)-OMOM). The reaction takes place in dichloromethane (DCM) in the presence of diisopropylethylamine (DIPEA) and tetrabutylammonium chloride (TBACl). Then, in step (c) compound 23 is reacted to the target compound 5D. The reaction is done in a mixture of tetrahydrofuran (THF), water and pyridine.

a) Synthesis of boc-3-iodo-D-Tyr-OH (22)

3-Iodo-D-Tyr-OH 11 (16.28 mmol) was dissolved in 150 ml of a mixture of THF/$H_2O$ (1:1) and TEA (4.44 ml, 32.56 mmol, 2 eq.) was added dropwise. The mixture was cooled on ice to 0° C. $Boc_2O$ (3.63 ml, 17.9 mmol, 1.1 eq.) was melt in the water bath at 30° C. and subsequently dissolved in 20 ml of THF. The solution was transferred to a dropping funnel and added dropwise over a period of 30 minutes. After one hour the ice bath was removed and the reaction mixture was stirred overnight at room temperature. The complete conversion was controlled by mans of HPLC. THF was removed in vacuum. The aqueous solution was adjusted to pH 3-4 with 1 M HCl and extracted three times with 150 ml of ethyl acetate each. The combined organic phases were dried over sodium sulphate and the solvent was removed in vacuum. The product was dried in high vacuum. The purity of the synthesis product (boc-3-iodo-D-Tyr-OH 22) was determined by HPLC (>95%).

b) Synthesis of boc-3-iodo-D-Tyr(MOM)-OMOM (23)

Boc-3-iodo-D-Tyr-OH 22 (16.28 mmol) was dissolved in 120 ml of dry DCM. DIPEA (5.67 ml, 32.56 mmol, 2 eq.) and tetrabutylammonium chloride (0.453 g, 1.63 mmol, 0.1 eq.) were added. A solution of methoxymethyl bromide (2.657 ml, 32.56 mmol, 2 eq.) in 30 ml of DCM (anhydrous) was slowly added dropwise to an ice-cooled solution of boc-3-iodo-D-Tyr-OH over a period of 30 minutes. After one hour the ice bath was removed and subsequently stirred overnight at room temperature. After having water added and subsequently separated and dried the organic phase the organic phase was evaporated in vacuum. Complete conversion was controlled by means of HPLC. The product boc-3-iodo-D-Tyr(MOM)-OMOM 23 was identified by HPLC (>95%).

c) Synthesis of boc-3-iodo-D-Tyr(MOM)-OH (5D)

Boc-I-D-Tyr(MOM)-OMOM was dissolved in 20 ml of THF. 20 ml of a 2 M solution of LiOH in water were added and stirred for 2 hours at room temperature. THF was removed in vacuum. 300 ml of DCM and 150 ml of a 5% $KHSO_4$ solution were added and stirred for 5 minutes. After phase separation the aqueous phase was extracted once with 150 ml of DCM. The combined organic phases were dried over $Na_2SO_4$ and the solvent was removed in vacuum. The product obtained was lyophilized.

$^1$H-NMR (400 MHz, $CDCl_3$) δ (ppm): 7.619 (s, 1H), 7.103 (d, 1H), 6.993 (d, 1H), 5.216 (s, 2H), 4.968; 4.54 (m, 1H), 3.504 (s, 3H), 3.138 (m, 1H), 2.993 (m, 1H), 1.440 (s, 9H).

Example 3 a) Synthesis of Tripeptides

To confirm the improved coupling properties of the compounds of general formula I-A according to the invention tripeptides have been prepared. The tripeptides prepared are shown in table 2, wherein Ac designates acetyl, Me methyl, Amb aminomethylbenzoyl and Pbf a 2,2,4,6,7-pentamethyldihydrobenzofurane-5-sulfonyl group.

For the preparation of the tripeptides P1 and P2 according to the invention either Fmoc-3-iodo-D-Tyr(MOM)-OH (compound 1D) or boc-3-iodo-D-Tyr(MOM)-OH (compound 5D) has been used. Moreover, for comparison tripeptides V1 and V2 have been prepared. Tripeptides V1 and V2 differ from tripetides P1 and P2 by the protection of the phenolic hydroxy group. In the tripetides P1 and P2 the phenolic hydroxy group is protected by a $-CH_2-O-CH_3$ group (MOM), while in tripeptides V1 and V2 it is not protected.

TABLE 2

| Compound | Structure | Designation (Sequence) |
|---|---|---|
| P1 | 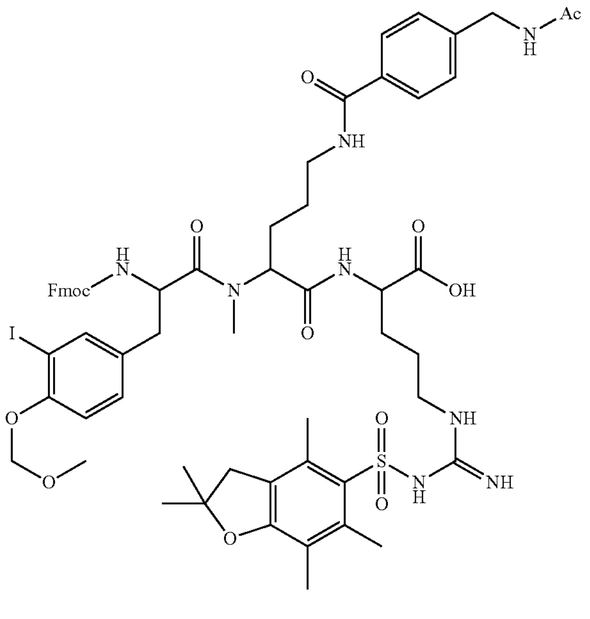 | Fmoc-3-iodo-D-Tyr(MOM)-N-Me-D-Orn(Amb-Ac)-Arg(Pbf)-OH |

TABLE 2-continued
| Compound | Structure | Designation (Sequence) |
| --- | --- | --- |
| V1 | 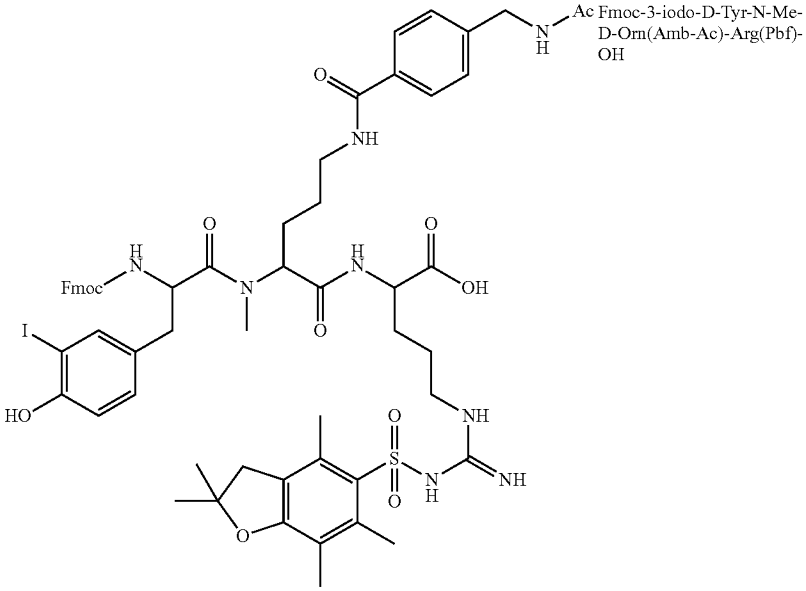 | Fmoc-3-iodo-D-Tyr-N-Me-D-Orn(Amb-Ac)-Arg(Pbf)-OH |
| P2 | 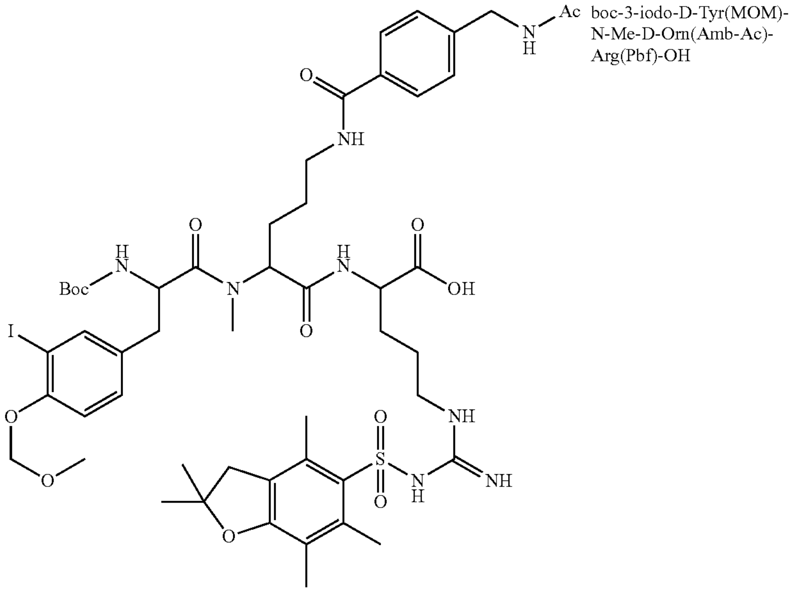 | boc-3-iodo-D-Tyr(MOM)-N-Me-D-Orn(Amb-Ac)-Arg(Pbf)-OH |

TABLE 2-continued

| Compound | Structure | Designation (Sequence) |
|---|---|---|
| V2 | 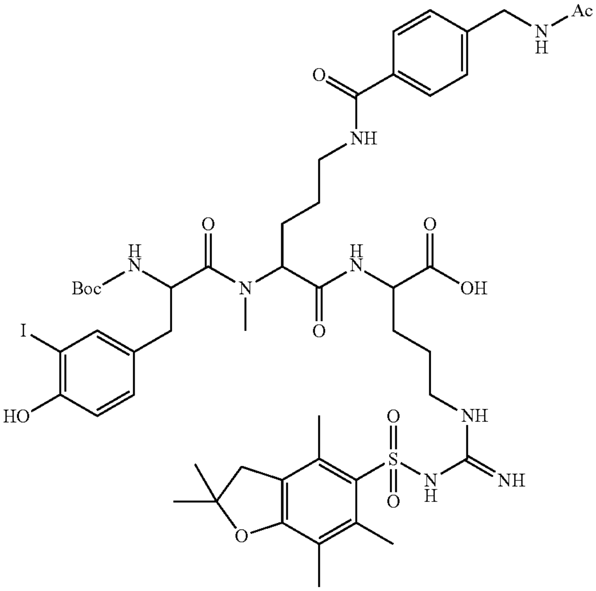 [SMILES: CC(=O)NCc1ccc(C(=O)NCCCC(C(=O)NC(CCCNC(=N)NS(=O)(=O)c2c(C)c(C)c3c(c2C)CC(C)(C)O3)C(=O)O)N(C)C(=O)C(Cc2ccc(O)c(I)c2)NC(=O)OC(C)(C)C)cc1] | boc-3-iodo-D-Tyr-N-Me-D-Orn(Amb-Ac)-Arg(Pbf)-OH |

The tripeptides have been prepared by means of the Fmoc/tBu strategy developed by Merrifield on a chlorotrityl resin which is also referred to as "Barlos resin" (Barlos, K., et al., Darstellung geschützter Peptid-Fragmente unter Einsatz substituierter Triphenylmethylharze, *Tetrahedron Letters,* 1989, 30(30), S. 3943-3946). This allows cleavage of completely protected peptide fragments by means of weakly acidic compounds such as hexafluoroisopropanol (HFIP). Coupling of all amino acid-like components is done by means of diisopropylcarbodiimide (DIC) and hydroxyiminocyano acetic ester (Oxyma). Cleavage of Fmoc-protective groups is done with 20% piperidine in DMF. Cleavage of the peptide from resin was done with 20% 1,1,1,3,3,3-hexafluoropropane-2-ol (HFIP) in DCM.

b) Comparison Tests

The tripeptides P1 and P2 according to the invention and the tripeptides V1 and V2 for comparison were coupled using diisopropylcarbodiimide (DIC) and hydroxyiminocyano acetic ester (Oxyma) within 60 min.

For the preparation of tripeptide P1 Fmoc-3-iodo-D-Tyr(MOM)-OH (1D) was coupled to H—N-Me-D-Orn(Amb-Ac)-Arg(Pbf) chlorotrityl resin. Coupling was kinetically monitored. The results are shown in table 3.

TABLE 3

Synthesis of Fmoc-3-iodo-D-Tyr(MOM)-N-Me-D-Orn(Amb-Ac)-Arg(Pbf)-OH (P1) from Fmoc-3-iodo-D-Tyr(MOM)-OH (1D) and H-N-Me-D-Orn(Amb-Ac)-Arg(Pbf) Chlorotrityl Resin

| Time (min) | Educt* (%) | Product P1 (%)** | Side Products (%) *** |
|---|---|---|---|
| 0 | 100 | 0 | 0 |
| 15 | 73 | 26 | 0 |
| 60 | 40 | 60 | 0 |

TABLE 3-continued

Synthesis of Fmoc-3-iodo-D-Tyr(MOM)-N-Me-D-Orn(Amb-Ac)-Arg(Pbf)-OH (P1) from Fmoc-3-iodo-D-Tyr(MOM)-OH (1D) and H-N-Me-D-Orn(Amb-Ac)-Arg(Pbf) Chlorotrityl Resin

| Time (min) | Educt* (%) | Product P1 (%)** | Side Products (%) *** |
|---|---|---|---|
| 120 | 14 | 86 | 0 |
| 720 | 6 | 94 | 0 |

*Educt is H-N-Me-D-Orn(Amb-Ac)-Arg(Pbf)-OH, since the reduction of Fmoc-3-iodo-D-Tyr(MOM)-OH can only be determined with some effort.
**Fmoc-3-iodo-D-Tyr(MOM)-N-Me-D-Orn(Amb-Ac)-Arg(Pbf)-OH (P1)
***It has not been determined which side products are involved.

For the preparation of tripeptide V1 Fmoc-3-iodo-D-Tyr-OH was coupled to H—N-Me-D-Orn(Amb-Ac)-Arg(Pbf) chlorotrityl resin. Coupling was kinetically monitored. The results are shown in table 4.

TABLE 4

Synthesis of Fmoc-3-iodo-D-Tyr-N-Me-D-Orn(Amb-Ac)-Arg(Pbf)-OH (V1) from Fmoc-3-iodo-D-Tyr-OH and H-N-Me-D-Orn(Amb-Ac)-Arg(Pbf) Chlorotrityl Resin

| Time (min) | Educt* (%) | Product V1 (%)** | Side Products (%)*** |
|---|---|---|---|
| 0 | 100 | 0 | 0 |
| 15 | 81 | 14.2 | 4.7 |
| 60 | 65.8 | 21.9 | 12.2 |
| 120 | 59.8 | 26 | 14.1 |
| 720 | 51.5 | 29 | 19.5 |

*Educt is H-N-Me-D-Orn(Amb-Ac)-Arg(Pbf)-OH, since the reduction of Fmoc-3-iodo-D-Tyr-OH can only be determined with some effort.
**Fmoc-3-iodo-D-Tyr-N-Me-D-Orn(Amb-Ac)-Arg(Pbf)-OH (V1)
***It has not been determined which side products are involved.

For the preparation of tripeptide P2 boc-3-iodo-D-Tyr(MOM)-OH (5D) was coupled to H—N-Me-D-Orn(Amb- Ac)-Arg(Pbf) chlorotrityl resin. Coupling was kinetically monitored. The results are shown in table 5.

TABLE 5

Synthesis of Boc-3-iodo-D-Tyr(MOM)-N-Me-D-Orn(Amb-Ac)-Arg(Pbf)-OH (P2) from Boc-3-iodo-D-Tyr(MOM)-OH and H-N-Me-D-Orn(Amb-Ac)-Arg(Pbf) Chlorotrityl Resin

| Time (min) | Educt* (%) | Product P2 (%)** | Side Products (%)*** |
|---|---|---|---|
| 0 | 100 | 0 | 0 |
| 15 | 87.3 | 12.17 | 0 |
| 60 | 37.16 | 62.84 | 0 |
| 120 | 13.37 | 86.63 | 0 |
| 720 | 0.68 | 99.32 | 0 |

*Educt is H-N-Me-D-Orn(Amb-Ac)-Arg(Pbf)-OH, since the reduction of boc-3-iodo-D-Tyr(MOM)-OH can only be determined with some effort.
**boc-3-iodo-D-Tyr(MOM)-N-Me-D-Orn(Amb-Ac)-Arg(Pbf)-OH (P2)
***It has not been determined which side products are involved.

For the preparation of tripeptide V2 boc-3-iodo-D-Tyr-OH was coupled to H—N-Me-D-Orn(Amb-Ac)-Arg(Pbf) chlorotrityl resin. Coupling was kinetically monitored. The results are shown in table 6.

TABLE 6

Synthesis of boc-3-iodo-D-Tyr-N-Me-D-Orn(Amb-Ac)-Arg(Pbf)-OH (V2) from boc-3-iodo-D-Tyr-OH and H-N-Me-D-Orn(Amb-Ac)-Arg(Pbf) Chlorotrityl Resin

| Time (min) | Educt* (%) | Product V2 (%)** | Side Products (%)*** |
|---|---|---|---|
| 0 | 100 | 0 | 0 |
| 15 | 93.2 | 5.7 | 1.06 |
| 60 | 73.3 | 16.1 | 10.6 |
| 120 | 65.2 | 19.8 | 15 |
| 720 | 53.74 | 18.56 | 27.7 |

*Educt is H-N-Me-D-Orn(Amb-Ac)-Arg(Pbf)-OH, since the reduction of boc-3-iodo-D-Tyr-OH can only be determined with some effort.
**boc-3-iodo-D-Tyr-N-Me-D-Orn(Amb-Ac)-Arg(Pbf)-OH
***It has not been determined which side products are involved.

Preparation of tripeptides P1 and P2 according to the invention and tripeptides V1 and V2 for comparison shows that both using Fmoc-3-iodo-D-Tyr(MOM)-OH (1D) and boc-3-iodo-D-Tyr(MOM)-OH (5D) results in the target compound of high purity and yield. Using the iodotyrosine derivatives that are unprotected in the side chain resulted in a significantly reduced yield and formation of non-specified side products. Tripeptides P1 and P2 give evidence for the increased efficiency of peptide synthesis resulting from the use of the tyrosine derivatives with protected phenolic hydroxy function according to the invention.

Example 4

Synthesis of Pentixather

Pentixather could be prepared with great efficiency by means of the amino acid Fmoc-3-iodo-D-Tyr(MOM)-OH (1D), while the use of the unprotected amino acid Fmoc-3-iodo-D-Tyr-OH resulted in no or only little conversion.

Example 5

Synthesis of PSMAI&T

Synthesis of the compound Glu-CO-Lys[(Sub)DLys-DPhe-DTyr(3I)-DOT-AGA]trifluoroacetate (PSMAI&T) (Wirtz, M., et al., *Synthesis and in vitro and in vivo evaluation of urea-based PSMA inhibitors with increased lipophilicity*. EJNMMI Research, 2018. 8(1): p. 84) run in analogy to the synthesis of pentixather with greater efficiency and significantly improved purity of the end product when using boc-3-iodo-D-Tyrosin(MOM)-OH (1D) instead of the unprotected derivative.

CITED LITERATURE

1. Sadri, K., et al., *Synthesis and biodoistribution studies of iodoine-*131 *D-amino acid YYK peptide as a potential therapeutic agent for labeling an anti-CD*20 *antibody*. 2009. 52(7): p. 289-294.
2. Hallaba, E., H. El-Asrag, and Y. Abou Zeid, 131*I-labelling of tyrosine by iodoine monochloride*. The International Journal of Applied Radiation and Isotopes, 1970. 21(2): p. 107-110.
3. Martin, E. B., et al., *Evaluation of the effect of D-amino acid incorporation into amyloid-reactive peptides*. Journal of translational medicine, 2017. 15(1): p. 247-247.
4. Assoian, R. K., et al., *Iodotyrosylation of peptides using tertiary-butyloxycarbonyl-l-*[125*I*]*iodootyrosine N-hydroxysuccinimide ester*. Analytical Biochemistry, 1980. 103(1): p. 70-76.
5. Schottelius, M., et al., [(177)*Lu*]*pentixather: Comprehensive Preclinical Characterization of a First CXCR*4*-directed Endoradiotherapeutic Agent*. Theranostics, 2017. 7(9): p. 2350-2362.
6. Brogsitter, C., et al., *Twins in spirit part II: DOTATATE and high-affinity DOTATATE—the clinical experience*. European journal of nuclear medicine and molecular imaging, 2014. 41.
7. Weineisen, M., et al., 68*Ga-and* 177*Lu-Labeled PSMA I&T: Optimization of a PSMA-Targeted Theranostic Concept and First Proof-of-Concept Human Studies*. J Nucl Med, 2015. 56(8): p. 1169-76.
8. A, W. M., *IODINATED INSULIN ANALOGUES WITH FORESHORTENED SIGNALING*. 14 Dec. 2016.
9. Schottelius, M., et al., *An optimized strategy for the mild and efficient solution phase iodoination of tyrosine residues in bioactive peptides*. Tetrahedron Letters, 2015. 56(47): p. 6602-6605.
10. Steer, A. M., et al., *A direct route for the preparation of Fmoc/OtBu protected iodootyrosine*. Tetrahedron Letters, 2018. 59(27): p. 2644-2646.
11. White, J. D. and J. C. Amedio, *Total synthesis of geodiamolide A, a novel cyclodepsipeptide of marine origin*. The Journal of Organic Chemistry, 1989. 54(4): p. 736-738.
12. Ishiwata, H., et al., *Total Synthesis of Doliculide, a Potent Cytotoxic Cyclodepsipeptide from the Japanese Sea Hare Dolabella auricularia*. The Journal of Organic Chemistry, 1994. 59(17): p. 4712-4713.
13. Pedersen, M. H. F. and L. Martiny, *Homogeneous deuteriodoeiodoination of iodoinated tyrosine in angiotensin-I using synthesized triethyl*[2*H*]*silane and Pd*(0). 2011. 54(4): p. 191-195.

The invention claimed is:

1. A compound of general formula I (formula I)

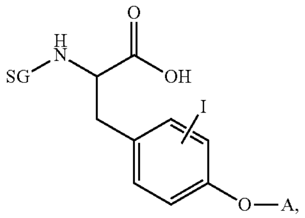

wherein

A is selected from the group consisting of an unbranched or branched alkyl group with 1 to 12 carbon atoms, an —$R^1$—O—$R^2$ group, an —$R^1$—Si($R^3R^4R^5$) group, an —$R^1$—O—Si($R^3R^4R^5$) group, a —C(O)—O—$R^9$—Si($R^3R^4R^5$) group, a —CH(O—$R^6$)(O—$R^7$) group, an —$R^1$—CH(O—$R^6$)(O—$R^7$) group, an —$R^1$—O—C(O)—O—$R^8$ group;

SG is a protective group;

$R^1$ is a divalent hydrocarbon residue with 1 to 12 carbon atoms;

$R^2$ is a monovalent hydrocarbon residue with 1 to 12 carbon atoms;

$R^3$, $R^4$ and $R^5$ each independently are a monovalent hydrocarbon residue with 1 to 12 carbon atoms;

$R^6$ and $R^7$ each independently are a monovalent hydrocarbon residue with 1 to 12 carbon atoms;

$R^8$ is a monovalent hydrocarbon residue with 1 to 12 carbon atoms; and $R^9$ is a divalent hydrocarbon residue with 1 to 12 carbon atoms.

2. The compound according to claim 1, wherein the compound is a compound of general formula I-A (formula I-A)

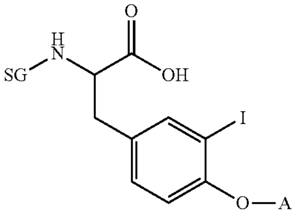

wherein A and SG have the meanings as previously defined.

3. The compound according to claim 1, wherein SG is selected from the group consisting of a fluorenylmethylenoxycarbonyl group (Fmoc), a tert-butoxycarbonyl group (boc), and a benzyloxycarbonyl group.

4. The compound according to claim 1, wherein A is selected from the group consisting of an unbranched or branched alkyl group with 1 to 12 carbon atoms, an —$R^1$—O—$R^2$ group, an —$R^1$—Si($R^3R^4R^5$) group, and a —C(O)—O—$R^9$—Si($R^3R^4R^5$) group, wherein $R^1$, $R^2$, $R^3$, $R^4$, $R^5$, and $R^9$ have the meanings as previously defined.

5. The compound according to claim 1, wherein A is selected from the group consisting of an alkyl group with 1 to 6 carbon atoms; an —$R^1$—O—$R^2$ group in which $R^1$ is an alkylene group with 1 to 6 carbon atoms and $R^2$ is an unbranched or branched alkyl group with 1 to 6 carbon atoms; an —$R^1$—Si($R^3R^4R^5$) group in which $R^1$ is an alkylene group with 1 to 6 carbon atoms and $R^3$, $R^4$ and $R^5$ each independently are an unbranched or branched alkyl group with 1 to 6 carbon atoms or an aryl group; and a —C(O)—O—$R^9$—Si($R^3R^4R^5$) group in which $R^9$ is an alkylene group with 1 to 6 carbon atoms and $R^3$, $R^4$ and $R^5$ each independently are an unbranched or branched alkyl group with 1 to 6 carbon atoms or an aryl group.

6. The compound according to claim 1, wherein A is selected from the group consisting of an alkyl group with 1 to 6 carbon atoms; an —$R^1$—O—$R^2$ group in which $R^1$ is an alkylene group with 1 to 4 carbon atoms and $R^2$ is an unbranched or branched alkyl group with 1 to 6 carbon atoms; an —$R^1$—Si($R^3R^4R^5$) group in which $R^1$ is an alkylene group with 1 to 4 carbon atoms and $R^3$, $R^4$ and $R^5$ each independently are an unbranched or branched alkyl group with 1 to 6 carbon atoms or an aryl group; and a —C(O)—O—$R^9$—Si($R^3R^4R^5$) group in which $R^9$ is an alkylene group with 1 to 6 carbon atoms and $R^3$, $R^4$ and $R^5$ each independently are an unbranched or branched alkyl group with 1 to 6 carbon atoms or an aryl group.

7. The compound according to claim 1, wherein the compound is 2-((((9H-fluoren-9-yl)methoxy)carbonyl)amino)-3-(3-iodo-4-(methoxy-methoxy)phenyl)propionic acid, 2-((((9H-fluoren-9-yl)methoxy)carbonyl)amino)-3-(3-iodo-4-(((2-(trimethylsilyl)ethoxy)carbonyl)oxy)phenyl)propionic acid, 2-((((9H-fluoren-9-yl)methoxy)carbonyl)amino)-3-(4-(2-(tert-butyldiphenylsilyl)ethoxy)-3-iodophenyl)propionic acid, or 2-((((9H-fluoren-9-yl)methoxy)carbonyl)amino)-3-(4-(tert-butoxy)-3-iodo-phenyl)propionic acid.

8. The compound according to claim 1, wherein the compound is 2-((tert-butoxycarbonyl)amino)-3-(3-iodo-4-(methoxymethoxy)phenyl)propionic acid, 2-((tert-butoxycarbonyl)amino)-3-(3-iodo-4-(((2-(trimethylsilyl)ethoxy)carbonyl)oxy)phenyl)propionic acid, 2-((tert-butoxycarbonyl)amino)-3-(4-(2-(tert-butyldiphenylsilyl)ethoxy)-3-iodophenyl)propionic acid, or 2-((tert-butoxycarbonyl)amino)-3-(4-(tert-butoxy)-3-iodophenyl)propionic acid.

9. A method for the preparation of the compound according to claim 1, comprising reacting a compound of general formula II (formula II)

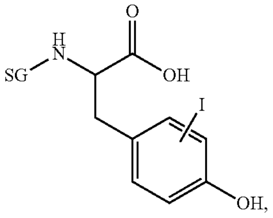

wherein SG is a protective group, with a compound of general formula X-A, wherein X is halogen or ammonium and A is selected from the group consisting of an unbranched or branched alkyl group with 1 to 12 carbon atoms, an —$R^1$—O—$R^2$ group, an —$R^1$—Si($R^3R^4R^5$) group, an —$R^1$—O—Si($R^3R^4R^5$)

group, a $—C(O)—O—R^9—Si(R^3R^4R^5)$ group, a $—CH(O—R^6)(O—R^7)$ group, an $—R^1—CH(O—R^6)(O—R^7)$ group, an $—R^1—O—C(O)—O—R^8$ group;

$R^1$ is a divalent hydrocarbon residue with 1 to 12 carbon atoms;

$R^2$ is a monovalent hydrocarbon residue with 1 to 12 carbon atoms;

$R^3$, $R^4$ and $R^5$ each independently are a monovalent hydrocarbon residue with 1 to 12 carbon atoms;

$R^6$ and $R^7$ each independently are a monovalent hydrocarbon residue with 1 to 12 carbon atoms;

$R^8$ is a monovalent hydrocarbon residue with 1 to 12 carbon atoms; and $R^9$ is a divalent hydrocarbon residue with 1 to 12 carbon atoms, to form a compound of general formula I (formula I)

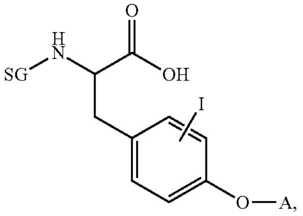

wherein A and SG have the meanings given in connection with formula II.

10. The method according to claim 9, wherein the compound of general formula II is reacted with a compound of general formula X-A to obtain a compound of general formula III (formula III)

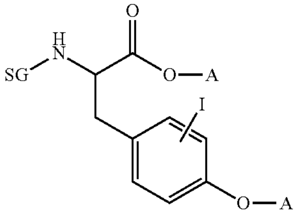

and subsequently the compound of general formula III is reacted to form a compound of general formula I.

11. The method according to claim 9, wherein the compound of general formula II is prepared from a compound of general formula IV (formula IV)

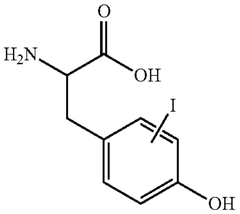

by introducing a protective group SG at the amino group of the compound of general formula IV.

* * * * *